United States Patent
Allesee

[19]

[11] Patent Number: 5,464,347
[45] Date of Patent: Nov. 7, 1995

[54] HYBRID ORTHODONTIC BRACKET SYSTEM AND METHOD

[76] Inventor: Timothy J. Allesee, 3909 Jamie La., Bloomington, Ind. 47401

[21] Appl. No.: 148,974

[22] Filed: Nov. 8, 1993

[51] Int. Cl.⁶ ........................................ A61C 3/00
[52] U.S. Cl. ........................................ 433/8; 433/16
[58] Field of Search .................... 433/8, 9, 10, 16, 433/17, 24

[56] References Cited

U.S. PATENT DOCUMENTS

| | | | |
|---|---|---|---|
| 2,386,124 | 10/1945 | Laskin | 433/20 X |
| 2,908,974 | 10/1959 | Stifter | 433/16 |
| 2,926,422 | 3/1960 | Wallshein | 433/8 |
| 3,203,098 | 8/1965 | Petraitis | 433/16 X |
| 3,477,128 | 11/1969 | Andrews | 433/16 |
| 3,660,900 | 5/1972 | Andrews | 433/16 |
| 4,161,066 | 7/1979 | Morrow et al. | 433/15 |
| 4,212,638 | 7/1980 | Korn | 433/8 |
| 4,219,617 | 8/1980 | Wallshein | 433/8 |
| 4,242,085 | 12/1980 | Wallshein | 433/16 X |
| 4,249,897 | 2/1981 | Anderson | 433/16 X |
| 4,337,037 | 6/1982 | Kurz | 433/8 |
| 4,353,692 | 10/1982 | Karrakussogiu | 433/16 |
| 4,386,908 | 6/1983 | Kurz | 433/8 X |
| 4,415,330 | 11/1983 | Daisley et al. | 433/16 |
| 4,487,581 | 12/1984 | Adler | 433/16 |
| 4,523,908 | 6/1985 | Drisaldi et al. | 433/8 |
| 4,529,382 | 7/1985 | Creekmore | 433/9 |
| 4,536,154 | 8/1985 | Garton, Jr. et al. | 433/8 |
| 4,575,337 | 3/1986 | Fujita | 433/8 |
| 4,585,413 | 4/1986 | Wool | 433/8 |
| 4,597,739 | 7/1986 | Rosenberg | 433/16 |
| 4,659,309 | 4/1987 | Merkel | 433/16 X |
| 4,676,746 | 6/1987 | Klapper | 433/16 |
| 4,793,804 | 12/1988 | Schudy | 433/8 |
| 4,819,316 | 4/1989 | Rossini et al. | 433/8 X |
| 4,850,865 | 7/1989 | Napolitano | 433/8 |
| 4,877,398 | 10/1989 | Kesling | 433/16 X |
| 4,897,036 | 1/1990 | Kesling | 433/20 X |
| 5,125,831 | 6/1992 | Pospisil | 433/8 |
| 5,161,969 | 11/1992 | Pospisil et al. | 433/8 |
| 5,174,753 | 12/1992 | Wool | 433/8 |
| 5,226,814 | 7/1993 | Allen | 43/8 X |
| 5,238,403 | 8/1993 | Schudy | 433/8 |
| 5,238,404 | 8/1993 | Andreiko | 433/20 |

*Primary Examiner*—Nicholas D. Lucchesi
*Attorney, Agent, or Firm*—Barnes & Thornburg

[57] ABSTRACT

An orthodontic bracket system includes a plurality of rectangular wires having a plurality of different sizes and a plurality of brackets. The plurality of brackets include an upper bicuspid bracket, an upper cuspid bracket, an upper lateral bracket, an upper central bracket, a lower bicuspid bracket, a lower cuspid bracket, and a lower anterior bracket. Each of the plurality of brackets includes a 0.020 inch width slot aligned at a selected torque angle for receiving the rectangular wire therein. The upper central bracket applies any actual torque force to an upper central tooth in a range of actual torque forces from about 0° to about +10°. The upper lateral bracket applies any actual torque force to an upper lateral tooth in a range of actual torque forces from about 0° to about +6°. The upper cuspid bracket applies any actual torque force to an upper cuspid tooth in a range of actual torque forces from about 4° to about +4°. The upper bicuspid bracket applies any actual torque force to an upper bicuspid tooth in a range of actual torque forces from about 0° to about −5°.

29 Claims, 19 Drawing Sheets

|  | ROTH | ANDREWS | WICK | HILGERS | BENCH | RICKETTS | CETLIN |
|---|---|---|---|---|---|---|---|
| U1 | +12 | +7 | +14 | +22 | +17 | +22 | +12 |
| U2 | +8 | +3 | +7 | +14 | +10 | +14 | +8 |
| U3 | −2 | −7 | −3 | +7 | +7 | +7 | −2 |
| U4 | −7 | −7 | −7 | −7 | −7 | 0 | −7 |
| U5 | −7 | −7 | −7 | −7 | −7 | 0 | −7 |
| L1 | −1 | −1 | −5 | −1 | −1 | 0 | 0 |
| L2 | −1 | −1 | −5 | −1 | −1 | 0 | 0 |
| L3 | −11 | −11 | −7 | +7 | +7 | +7 | −5 |
| L4 | −17 | −17 | −11 | −11 | −11 | 0 | −11 |
| L5 | −22 | −22 | −17 | −17 | −22 | −14 | −17 |

FIG. 5a

|  | ROTH | ANDREWS | WICK | HILGERS | BENCH | RICKETTS | CETLIN |
|---|---|---|---|---|---|---|---|
| U1 | 5 | 5 | 5 | 5 | 5 | 0 | 5 |
| U2 | 9 | 9 | 8 | 8 | 9 | 8 | 9 |
| U3 | 13 | 11 | 10 | 10 | 9 | 5 | 7 |
| U4, U5 | 0 | 0 | 0 | 0 | 0 | 0 | 0 |
| L1, L2 | 0 | 0 | 0 | 0 | 2 | 0 | 0 |
| L3 | 7 | 5 | 6 | 5 | 5 | 5 | 7 |
| L4, L5 | 0 | 0 | 0 | 0 | 0 | 0 | 0 |

FIG. 5b

THE HYBRID EDGEWISE SYSTEM

|  | U1 | U2 | U3 | U4 | U5 |
|---|---|---|---|---|---|
| Torque | +17 | +12 | +7/−7* | −7 | −11** |
| Angulation | +5 | +8 | +10 | 0 | 0 |
| Anti-rotation | 0 | 0 | 0 | 0 | 0 |
| In-out | Standard | Thickest | Thin | Thin | Thin |

|  | L1 | L2 | L3 | L4 | L5 |
|---|---|---|---|---|---|
| Torque | 0 | 0 | +7/−7* | −17** | −22 |
| Angulation | 0 | 0 | +5 | 0 | 0 |
| Anti-rotation | 0 | 0 | 0 | 0 | 0 |
| In-out | Thickest | Thickest | Thin | Thin | Thin |

FIG. 8

EXTRACTION BRACKET SERIES

|  | U3 | L3 |
|---|---|---|
| Torque | −4 | −11 |
| Angulation | +14 | +7 |
| Anti-rotation | 6 | 6 |
| In-out | Thin | Thin |
| Ball hooks | Yes | Yes |

FIG. 9

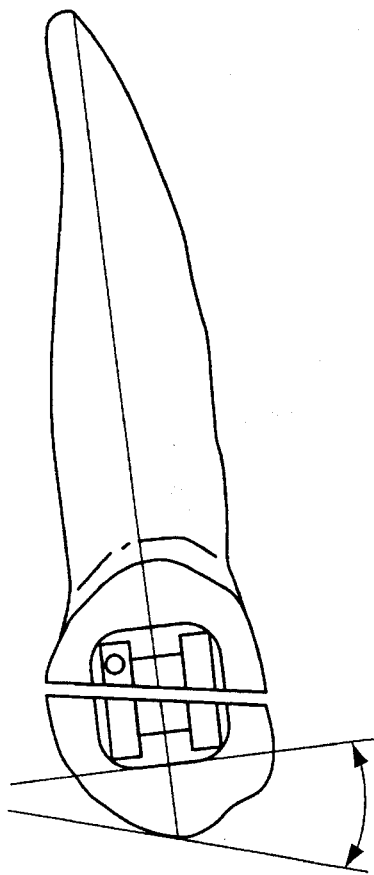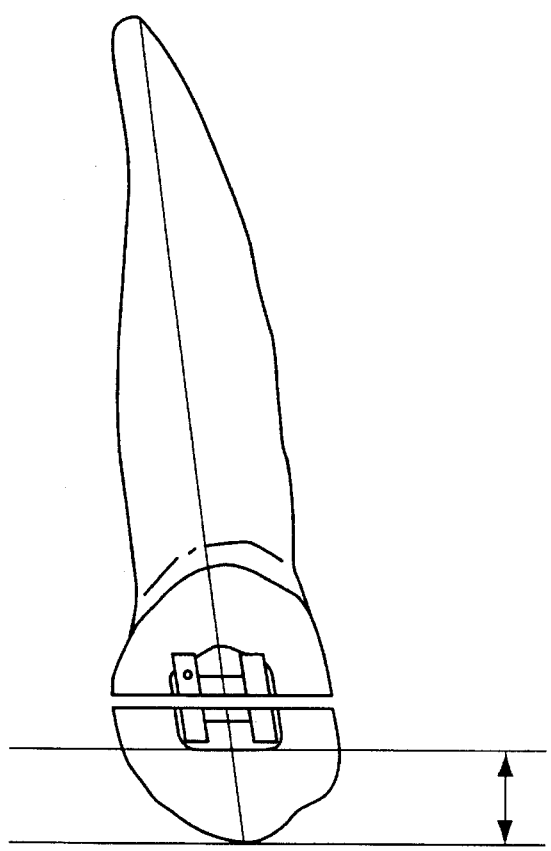
FIG. 12  FIG. 13

TORQUE ANGLE FORMED IN BRACKET - .020 SLOT

| WIRE SIZE | DEFLECTION ANGLE | 1° | 2° | 3° | 5° | 7° | 8° | 9° | 10° | 11° |
|---|---|---|---|---|---|---|---|---|---|---|
| 014 x 014 | - 8.151 | 0 | 0 | 0 | 0 | 0 | 0 | 0 | 0 | 0 |
| 014 x 018 | - 23.4145 | 0 | 0 | 0 | 0 | 0 | 0 | 0 | 0 | 0 |
| 014 x 022 | - 17.6109 | 0 | 0 | 0 | 0 | 0 | 0 | 0 | 0 | 0 |
| 014 x 025 | - 15.0183 | 0 | 0 | 0 | 0 | 0 | 0 | 0 | 0 | 0 |
| 014 x 028 | - 13.143 | 0 | 0 | 0 | 0 | 0 | 0 | 0 | 0 | 0 |
| 015 x 015 | - 25.5288 | 0 | 0 | 0 | 0 | 0 | 0 | 0 | 0 | 0 |
| 015 x 018 | - 18.7976 | 0 | 0 | 0 | 0 | 0 | 0 | 0 | 0 | 0 |
| 015 x 022 | - 14.4002 | 0 | 0 | 0 | 0 | 0 | 0 | 0 | 0 | 0 |
| 015 x 025 | - 12.3501 | 0 | 0 | 0 | 0 | 0 | 0 | 0 | 0 | 0 |
| 015 x 028 | - 10.8441 | 0 | 0 | 0 | 0 | 0 | 0 | 0 | 0 | 0.15 |
| 016 x 018 | - 14.5119 | 0 | 0 | 0 | 0 | 0 | 0 | 0 | 0 | 0 |
| 016 x 016 | - 17.1144 | 0 | 0 | 0 | 0 | 0 | 0 | 0 | 0 | 0 |
| 016 x 022 | - 11.298 | 0 | 0 | 0 | 0 | 0 | 0 | 0 | 0 | 0 |
| 016 x 025 | - 9.74312 | 0 | 0 | 0 | 0 | 0 | 0 | 0 | 0 | 1.25 |
| 016 x 028 | - 8.58394 | 0 | 0 | 0 | 0 | 0 | 0 | 0.41 | 0.25 | 2.41 |
| 017 x 017 | - 11.2934 | 0 | 0 | 0 | 0 | 0 | 0 | 0 | 1.41 | 0 |
| 017 x 022 | - 8.3066 | 0 | 0 | 0 | 0 | 0 | 0 | 0 | 0 | 2.69 |
| 017 x 025 | - 7.20182 | 0 | 0 | 0 | 0 | 0 | 0.80 | 0.69 | 1.69 | 3.80 |
| 017 x 028 | - 6.36646 | 0 | 0 | 0 | 0 | 0.63 | 1.63 | 1.80 | 2.80 | 4.63 |
| 0175 x 0175 | - 8.91285 | 0 | 0 | 0 | 0 | 0 | 0 | 2.63 | 3.63 | |
| 0175 x 022 | - 6.85281 | 0 | 0 | 0 | 0 | 0.14 | 0 | 0.08 | 1.08 | 2.08 |
| 0175 x 025 | - 5.95687 | 0 | 0 | 0 | 0 | 1.04 | 1.14 | 2.14 | 3.14 | 4.14 |
| 0175 x 028 | - 5.27479 | 0 | 0 | 0 | 0 | 1.72 | 2.04 | 3.04 | 4.04 | 5.04 |
| 018 x 018 | - 6.78308 | 0 | 0 | 0 | 0 | 0.21 | 2.72 | 3.72 | 4.72 | 5.72 |
| 018 x 022 | - 5.42695 | 0 | 0 | 0 | 0 | 1.57 | 1.21 | 2.21 | 3.21 | 4.21 |
| 018 x 025 | - 4.72449 | 0 | 0 | 0 | 0.27 | 2.27 | 2.57 | 3.57 | 4.57 | 5.57 |
| 018 x 028 | - 4.19498 | 0 | 0 | 0 | 0.80 | 2.80 | 3.27 | 4.27 | 5.27 | 6.27 |
| | | | | | | | 3.80 | 4.80 | 5.80 | 6.80 |
| 019 x 019 | - 3.10098 | 0 | 0 | 0 | 1.90 | 3.90 | 4.90 | 5.90 | 6.90 | 7.90 |
| 019 x 025 | - 2.32842 | 0 | 0 | 0.67 | 2.67 | 4.67 | 5.67 | 6.67 | 7.67 | 8.67 |
| 019 x 028 | - 2.07215 | 0 | 0 | 0.93 | 2.93 | 4.93 | 5.93 | 6.93 | 7.93 | 8.93 |
| 0195 x 0195 | - 1.48863 | 0 | 0.51 | 1.51 | 3.51 | 5.51 | 6.51 | 7.51 | 8.51 | 9.51 |
| 0195 x 025 | - 1.15508 | 0 | 0.84 | 1.84 | 3.84 | 5.84 | 6.84 | 7.84 | 8.84 | 9.84 |
| 0195 x 028 | - 1.02964 | 0 | 0.97 | 1.97 | 3.97 | 5.97 | 6.97 | 7.97 | 8.97 | 9.97 |

FIG. 14a                    ACTUAL TORQUE FORCES

TORQUE ANGLE FORMED IN BRACKET - .020 SLOT

| WIRE SIZE | DEFLECTION ANGLE | 12° | 14° | 15° | 17° | 20° | 22° | 25° | 27° | 30° |
|---|---|---|---|---|---|---|---|---|---|---|
| 014 x 014 | 8.151 | 0 | 0 | 0 | 0 | 0 | 0 | 0 | 0 | 0 |
| 014 x 018 | 23.4145 | 0 | 0 | 0 | 0 | 0 | 0 | 1.58 | 3.58 | 6.58 |
| 014 x 022 | 17.6109 | 0 | 0 | 0 | 0 | 2.39 | 4.39 | 7.39 | 9.39 | 12.39 |
| 014 x 025 | 15.0183 | 0 | 0 | 0 | 1.98 | 4.98 | 6.98 | 9.98 | 11.98 | 14.98 |
| 014 x 028 | 13.143 | 0 | 0.85 | 1.85 | 3.85 | 6.85 | 8.85 | 11.85 | 13.85 | 16.85 |
| 015 x 015 | 25.5288 | 0 | 0 | 0 | 0 | 0 | 0 | 0 | 1.47 | 4.47 |
| 015 x 018 | 18.7976 | 0 | 0 | 0 | 0 | 1.20 | 3.20 | 6.20 | 8.20 | 11.20 |
| 015 x 022 | 14.4002 | 0 | 0 | 0.60 | 2.60 | 5.60 | 7.60 | 10.60 | 12.60 | 15.60 |
| 015 x 025 | 12.3501 | 0 | 1.65 | 2.65 | 4.65 | 7.65 | 9.65 | 12.65 | 14.65 | 17.65 |
| 015 x 028 | 10.8441 | 1.15 | 3.15 | 4.15 | 6.15 | 9.15 | 11.15 | 14.15 | 16.15 | 19.15 |
| 016 x 018 | 14.5119 | 0 | 0 | 0.49 | 2.49 | 5.49 | 7.49 | 10.49 | 12.49 | 15.49 |
| 016 x 016 | 17.1144 | 0 | 0 | 0 | 0 | 2.88 | 4.88 | 7.88 | 9.88 | 12.88 |
| 016 x 022 | 11.298 | 0.70 | 2.70 | 3.70 | 5.70 | 8.70 | 10.70 | 13.70 | 15.70 | 18.70 |
| 016 x 025 | 9.74312 | 2.25 | 4.25 | 5.25 | 7.25 | 10.25 | 12.25 | 15.25 | 17.25 | 20.25 |
| 016 x 028 | 8.58394 | 3.41 | 5.41 | 6.41 | 8.41 | 11.41 | 13.41 | 16.41 | 18.41 | 21.41 |
| 017 x 017 | 11.2934 | 0.70 | 2.70 | 3.70 | 5.70 | 8.70 | 10.70 | 13.70 | 15.70 | 18.70 |
| 017 x 022 | 8.3066 | 3.69 | 5.69 | 6.69 | 8.69 | 11.69 | 13.69 | 16.69 | 18.69 | 21.69 |
| 017 x 025 | 7.20182 | 4.80 | 6.80 | 7.80 | 9.80 | 12.80 | 14.80 | 17.80 | 19.80 | 22.80 |
| 017 x 028 | 6.36646 | 5.63 | 7.63 | 8.63 | 10.63 | 13.63 | 15.63 | 18.63 | 20.63 | 23.63 |
| 0175 x 0175 | 8.91285 | 3.08 | 5.08 | 6.08 | 8.08 | 11.08 | 13.08 | 16.08 | 18.08 | 21.08 |
| 0175 x 022 | 6.85281 | 5.14 | 7.14 | 8.14 | 10.14 | 13.14 | 15.14 | 18.14 | 20.14 | 23.14 |
| 0175 x 025 | 5.95687 | 6.04 | 8.04 | 9.04 | 11.04 | 14.04 | 16.04 | 19.04 | 21.04 | 24.04 |
| 0175 x 028 | 5.27479 | 6.72 | 8.72 | 9.72 | 11.72 | 14.72 | 16.72 | 19.72 | 21.72 | 24.72 |
| 018 x 018 | 6.78308 | 5.21 | 7.21 | 8.21 | 10.21 | 13.21 | 15.21 | 18.21 | 20.21 | 23.21 |
| 018 x 022 | 5.42695 | 6.57 | 8.57 | 9.57 | 11.57 | 14.57 | 16.57 | 19.57 | 21.57 | 24.57 |
| 018 x 025 | 4.72449 | 7.27 | 9.27 | 10.27 | 12.27 | 15.27 | 17.27 | 20.27 | 22.27 | 25.27 |
| 018 x 028 | 4.19498 | 7.80 | 9.80 | 10.80 | 12.80 | 15.80 | 17.80 | 20.80 | 22.80 | 25.80 |
| 019 x 019 | 3.10098 | 8.90 | 10.90 | 11.90 | 13.90 | 16.90 | 18.90 | 21.90 | 23.90 | 26.90 |
| 019 x 025 | 2.32842 | 9.67 | 11.67 | 12.67 | 14.67 | 17.67 | 19.67 | 22.67 | 24.67 | 27.67 |
| 019 x 028 | 2.07215 | 9.93 | 11.93 | 12.93 | 14.93 | 17.93 | 19.93 | 22.93 | 24.93 | 27.93 |
| 0195 x 0195 | 1.48863 | 10.51 | 12.51 | 13.51 | 15.51 | 18.51 | 20.51 | 23.51 | 25.51 | 28.51 |
| 0195 x 025 | 1.15508 | 10.84 | 12.84 | 13.84 | 15.84 | 18.84 | 20.84 | 23.84 | 25.84 | 28.84 |
| 0195 x 028 | 1.02964 | 10.97 | 12.97 | 13.97 | 15.97 | 18.97 | 20.97 | 23.97 | 25.97 | 28.97 |

FIG. 14b     ACTUAL TORQUE FORCES

TORQUE ANGLE FORMED IN BRACKET - .018 SLOT

| WIRE SIZE | DEFLECTION ANGLE | 1° | 2° | 3° | 5° | 7° | 8° | 9° | 10° | 11° |
|---|---|---|---|---|---|---|---|---|---|---|
| 014 x 014 | 20.3864 | 0 | 0 | 0 | 0 | 0 | 0 | 0 | 0 | 0 |
| 014 x 018 | 14.25 | 0 | 0 | 0 | 0 | 0 | 0 | 0 | 0 | 0 |
| 014 x 022 | 11.1802 | 0 | 0 | 0 | 0 | 0 | 0 | 0 | 0 | 0 |
| 014 x 025 | 9.66844 | 0 | 0 | 0 | 0 | 0 | 0 | 0 | 0.33 | 1.33 |
| 014 x 028 | 8.5338 | 0 | 0 | 0 | 0 | 0 | 0 | 0.46 | 1.46 | 2.46 |
| 015 x 015 | 13.0519 | 0 | 0 | 0 | 0 | 0 | 0 | 0 | 0 | 0 |
| 015 x 018 | 10.3889 | 0 | 0 | 0 | 0 | 0 | 0 | 0 | 0 | 0.61 |
| 015 x 022 | 8.2453 | 0 | 0 | 0 | 0 | 0 | 0 | 0.75 | 1.75 | 2.75 |
| 015 x 025 | 7.16329 | 0 | 0 | 0 | 0 | 0 | 0.84 | 1.84 | 2.84 | 3.84 |
| 015 x 028 | 6.33945 | 0 | 0 | 0 | 0 | 0.66 | 1.66 | 2.66 | 3.66 | 4.66 |
| 016 x 016 | 7.70205 | 0 | 0 | 0 | 0 | 0 | 0.30 | 1.30 | 2.30 | 3.30 |
| 016 x 018 | 6.73292 | 0 | 0 | 0 | 0 | 0.26 | 1.26 | 2.26 | 3.26 | 4.26 |
| 016 x 022 | 5.40176 | 0 | 0 | 0 | 0 | 1.60 | 2.60 | 3.60 | 4.60 | 5.60 |
| 016 x 025 | 4.71296 | 0 | 0 | 0 | 0.28 | 2.28 | 3.28 | 4.28 | 5.28 | 6.28 |
| 016 x 028 | 4.18351 | 0 | 0 | 0 | 0.81 | 2.81 | 3.81 | 4.81 | 5.81 | 6.81 |
| 017 x 017 | 3.47801 | 0 | 0 | 0 | 1.52 | 3.52 | 4.52 | 5.52 | 6.52 | 7.52 |
| 017 x 022 | 2.65275 | 0 | 0 | 0.34 | 2.34 | 4.34 | 5.34 | 6.34 | 7.34 | 8.34 |
| 017 x 025 | 2.32453 | 0 | 0 | 0.67 | 2.67 | 4.67 | 5.67 | 6.67 | 7.67 | 8.67 |
| 017 x 028 | 2.06942 | 0 | 0 | 0.93 | 2.93 | 4.93 | 5.93 | 6.93 | 7.93 | 8.93 |
| 0175 x 0175 | 1.66134 | 0 | 0.34 | 1.34 | 3.34 | 5.34 | 6.34 | 7.34 | 8.34 | 9.34 |
| 0175 x 022 | 1.31428 | 0 | 0.68 | 1.68 | 3.68 | 5.68 | 6.68 | 7.68 | 8.68 | 9.68 |
| 0175 x 025 | 1.15413 | 0 | 0.84 | 1.84 | 3.84 | 5.84 | 6.84 | 7.84 | 8.84 | 9.84 |
| 0175 x 028 | 1.02897 | 0 | 0.97 | 1.97 | 3.97 | 5.97 | 6.97 | 7.97 | 8.97 | 9.97 |

ACTUAL TORQUE FORCES

FIG. 15a

TORQUE ANGLE FORMED IN BRACKET - .018 SLOT

| WIRE SIZE | DEFLECTION ANGLE | 12° | 14° | 15° | 17° | 22° | 25° | 27° | 30° |
|---|---|---|---|---|---|---|---|---|---|
| 014 x 014 | -20.3864 | 0 | 0 | 0 | 0 | 1.61 | 4.61 | 6.61 | 9.61 |
| 014 x 018 | -14.25 | 0 | 0 | 0.75 | 2.75 | 7.75 | 10.75 | 12.75 | 15.75 |
| 014 x 022 | -11.1802 | 0.81 | 2.81 | 3.81 | 5.81 | 10.81 | 13.81 | 15.81 | 18.81 |
| 014 x 025 | -9.66844 | 2.33 | 4.33 | 5.33 | 7.33 | 12.33 | 15.33 | 17.33 | 20.33 |
| 014 x 028 | -8.5338 | 3.46 | 5.46 | 6.46 | 8.46 | 13.46 | 16.46 | 18.46 | 21.46 |
| 015 x 015 | -13.0519 | 0 | 0.95 | 1.95 | 3.95 | 8.95 | 11.95 | 13.95 | 16.95 |
| 015 x 018 | -10.3889 | 1.61 | 3.61 | 4.61 | 6.61 | 11.61 | 14.61 | 16.61 | 19.61 |
| 015 x 022 | -8.2453 | 3.75 | 5.75 | 6.75 | 8.75 | 13.75 | 16.75 | 18.75 | 21.75 |
| 015 x 025 | -7.16329 | 4.84 | 6.84 | 7.84 | 9.84 | 14.84 | 17.84 | 19.84 | 22.84 |
| 015 x 028 | -6.33945 | 5.66 | 7.66 | 8.66 | 10.66 | 15.66 | 18.66 | 20.66 | 23.66 |
| 016 x 016 | -7.70205 | 4.30 | 6.30 | 7.30 | 9.30 | 14.30 | 17.30 | 19.30 | 22.30 |
| 016 x 018 | -6.73292 | 5.26 | 7.26 | 8.26 | 10.26 | 15.26 | 18.26 | 20.26 | 23.26 |
| 016 x 022 | -5.40176 | 6.60 | 8.60 | 9.60 | 11.60 | 16.60 | 19.60 | 21.60 | 24.60 |
| 016 x 025 | -4.71296 | 7.28 | 9.28 | 10.28 | 12.28 | 17.28 | 20.28 | 22.28 | 25.28 |
| 016 x 028 | -4.18351 | 7.81 | 9.81 | 10.81 | 12.81 | 17.81 | 20.81 | 22.81 | 25.81 |
| 017 x 017 | -3.47801 | 8.52 | 10.52 | 11.52 | 13.52 | 18.52 | 21.52 | 23.52 | 26.52 |
| 017 x 022 | -2.65275 | 9.34 | 11.34 | 12.34 | 14.34 | 19.34 | 22.34 | 24.34 | 27.34 |
| 017 x 025 | -2.32453 | 9.67 | 11.67 | 12.67 | 14.67 | 19.67 | 22.67 | 24.67 | 27.67 |
| 017 x 028 | -2.06942 | 9.93 | 11.93 | 12.93 | 14.93 | 19.93 | 22.93 | 24.93 | 27.93 |
| 0175 x 0175 | -1.66134 | 10.34 | 12.34 | 13.34 | 15.34 | 20.34 | 23.34 | 25.34 | 28.34 |
| 0175 x 022 | -1.31428 | 10.68 | 12.68 | 13.68 | 15.68 | 20.68 | 23.68 | 25.68 | 28.68 |
| 0175 x 025 | -1.15413 | 10.84 | 12.84 | 13.84 | 15.84 | 20.84 | 23.84 | 25.84 | 28.84 |
| 0175 x 028 | -1.02897 | 10.97 | 12.97 | 13.97 | 15.97 | 20.97 | 23.97 | 25.97 | 28.97 |

ACTUAL TORQUE FORCES

FIG. 15b

TORQUE ANGLE FORMED IN BRACKET - .022 SLOT

| WIRE SIZE | DEFLECTION ANGLE | 1° | 2° | 3° | 5° | 7° | 8° | 9° | 10° | 11° |
|---|---|---|---|---|---|---|---|---|---|---|
| 016 x 016 | 31.4759 | 0 | 0 | 0 | 0 | 0 | 0 | 0 | 0 | 0 |
| 016 x 022 | 17.9453 | 0 | 0 | 0 | 0 | 0 | 0 | 0 | 0 | 0 |
| 016 x 025 | 15.2144 | 0 | 0 | 0 | 0 | 0 | 0 | 0 | 0 | 0 |
| 016 x 028 | 13.2702 | 0 | 0 | 0 | 0 | 0 | 0 | 0 | 0 | 0 |
| 017 x 017 | 21.217 | 0 | 0 | 0 | 0 | 0 | 0 | 0 | 0 | 0 |
| 017 x 022 | 14.6115 | 0 | 0 | 0 | 0 | 0 | 0 | 0 | 0 | 0 |
| 017 x 025 | 12.4778 | 0 | 0 | 0 | 0 | 0 | 0 | 0 | 0 | 0 |
| 017 x 028 | 10.9284 | 0 | 0 | 0 | 0 | 0 | 0 | 0 | 0 | 0.07 |
| 0175 x 0175 | 17.7396 | 0 | 0 | 0 | 0 | 0 | 0 | 0 | 0 | 0 |
| 0175 x 022 | 12.9987 | 0 | 0 | 0 | 0 | 0 | 0 | 0 | 0 | 0 |
| 0175 x 025 | 11.1388 | 0 | 0 | 0 | 0 | 0 | 0 | 0 | 0 | 0 |
| 0175 x 028 | 9.7755 | 0 | 0 | 0 | 0 | 0 | 0 | 0 | 0.22 | 1.22 |
| 018 x 018 | 14.7962 | 0 | 0 | 0 | 0 | 0 | 0 | 0 | 0 | 0 |
| 018 x 022 | 11.4212 | 0 | 0 | 0 | 0 | 0 | 0 | 0 | 0 | 0 |
| 018 x 025 | 9.81971 | 0 | 0 | 0 | 0 | 0 | 0 | 0.36 | 0.18 | 1.18 |
| 018 x 028 | 8.6353 | 0 | 0 | 0 | 0 | 0 | 0.75 | 0.63 | 1.36 | 2.36 |
| 019 x 019 | 9.96038 | 0 | 0 | 0 | 0 | 0 | 0 | 0 | 0.04 | 1.04 |
| 019 x 022 | 8.36983 | 0 | 0 | 0 | 0 | 0.10 | 1.10 | 1.75 | 1.63 | 2.63 |
| 019 x 025 | 7.24215 | 0 | 0 | 0 | 0 | 1.01 | 2.01 | 3.01 | 2.75 | 3.75 |
| 019 x 028 | 6.39394 | 0 | 0 | 0 | 0 | 1.70 | 2.70 | 3.70 | 3.60 | 4.60 |
| 0195 x 0195 | 7.91687 | 0 | 0 | 0 | 0 | 0 | 0.08 | 1.08 | 2.08 | 3.08 |
| 0195 x 022 | 6.89477 | 0 | 0 | 0 | 0 | 0.10 | 1.10 | 2.10 | 3.10 | 4.10 |
| 0195 x 025 | 5.98397 | 0 | 0 | 0 | 0 | 1.01 | 2.01 | 3.01 | 4.01 | 5.01 |
| 0195 x 028 | 5.29339 | 0 | 0 | 0 | 0 | 1.70 | 2.70 | 3.70 | 4.70 | 5.70 |
| 020 x 020 | 6.06118 | 0 | 0 | 0 | 0 | 0.94 | 1.94 | 2.94 | 3.94 | 4.94 |
| 0215 x 0215 | 1.34845 | 0 | 0.65 | 1.65 | 3.65 | 5.65 | 6.65 | 7.65 | 8.65 | 9.65 |
| 0215 x 028 | 1.03031 | 0 | 0.97 | 1.97 | 3.97 | 5.97 | 6.97 | 7.97 | 8.97 | 9.97 |
| 021 x 025 | 2.3323 | 0 | 0 | 0.67 | 2.67 | 4.67 | 5.67 | 6.67 | 7.67 | 8.67 |
| 021 x 028 | 2.0749 | 0 | 0 | 0.93 | 2.93 | 4.93 | 5.93 | 6.93 | 7.93 | 8.93 |

FIG. 16a  ACTUAL TORQUE FORCES

TORQUE ANGLE FORMED IN BRACKET - .022 SLOT

| WIRE SIZE | DEFLECTION ANGLE | 12° | 14° | 15° | 17° | 22° | 25° | 27° | 30° |
|---|---|---|---|---|---|---|---|---|---|
| 016 x 016 | 31.4759 | 0 | 0 | 0 | 0 | 0 | 0 | 0 | 0 |
| 016 x 022 | 17.9453 | 0 | 0 | 0 | 0 | 4.05 | 7.05 | 9.05 | 12.05 |
| 016 x 025 | 15.2144 | 0 | 0 | 0 | 1.78 | 6.78 | 9.78 | 11.78 | 14.78 |
| 016 x 028 | 13.2702 | 0 | 0.73 | 1.73 | 3.73 | 8.73 | 11.73 | 13.73 | 16.73 |
| 017 x 017 | 21.217 | 0 | 0 | 0 | 0 | 0.78 | 3.78 | 5.78 | 8.78 |
| 017 x 022 | 14.6115 | 0 | 0 | 0.39 | 2.39 | 7.39 | 10.39 | 12.39 | 15.39 |
| 017 x 025 | 12.4778 | 0 | 1.52 | 2.52 | 4.52 | 9.52 | 12.52 | 14.52 | 17.52 |
| 017 x 028 | 10.9284 | 1.07 | 3.07 | 4.07 | 6.07 | 11.07 | 14.07 | 16.07 | 19.07 |
| 0175 x 0175 | 17.7396 | 0 | 0 | 0 | 0 | 4.26 | 7.26 | 9.26 | 12.26 |
| 0175 x 022 | 12.9987 | 0 | 1.00 | 2.00 | 4.00 | 9.00 | 12.00 | 14.00 | 17.00 |
| 0175 x 025 | 11.1388 | 0.86 | 2.86 | 3.86 | 5.86 | 10.86 | 13.86 | 15.86 | 18.86 |
| 0175 x 028 | 9.7755 | 2.22 | 4.22 | 5.22 | 7.22 | 12.22 | 15.22 | 17.22 | 20.22 |
| 018 x 018 | 14.7962 | 0 | 0 | 0.20 | 2.20 | 7.20 | 10.20 | 12.20 | 15.20 |
| 018 x 022 | 11.4212 | 0.58 | 2.58 | 3.58 | 5.58 | 10.58 | 13.58 | 15.58 | 18.58 |
| 018 x 025 | 9.81971 | 2.18 | 4.18 | 5.18 | 7.18 | 12.18 | 15.18 | 17.18 | 20.18 |
| 018 x 028 | 8.6353 | 3.36 | 5.36 | 6.36 | 8.36 | 13.36 | 16.36 | 18.36 | 21.36 |
| 019 x 019 | 9.96038 | 2.04 | 4.04 | 5.04 | 7.04 | 12.04 | 15.04 | 17.04 | 20.04 |
| 019 x 022 | 8.36983 | 3.63 | 5.63 | 6.63 | 8.63 | 13.63 | 16.63 | 18.63 | 21.63 |
| 019 x 025 | 7.24215 | 4.75 | 6.75 | 7.75 | 9.75 | 14.75 | 17.75 | 19.75 | 22.75 |
| 019 x 028 | 6.39394 | 5.60 | 7.60 | 8.60 | 10.60 | 15.60 | 18.60 | 20.60 | 23.60 |
| 0195 x 0195 | 7.91687 | 4.08 | 6.08 | 7.08 | 9.08 | 14.08 | 17.08 | 19.08 | 22.08 |
| 0195 x 022 | 6.89477 | 5.10 | 7.10 | 8.10 | 10.10 | 15.10 | 18.10 | 20.10 | 23.10 |
| 0195 x 025 | 5.98397 | 5.01 | 8.01 | 9.01 | 11.01 | 16.01 | 19.01 | 21.01 | 24.01 |
| 0195 x 028 | 5.29339 | 6.70 | 8.70 | 9.70 | 11.70 | 16.70 | 19.70 | 21.70 | 24.70 |
| 020 x 020 | 6.06118 | 5.94 | 7.94 | 8.94 | 10.94 | 15.94 | 18.94 | 20.94 | 23.94 |
| 0215 x 0215 | 1.34845 | 10.65 | 12.65 | 13.65 | 15.65 | 20.65 | 23.65 | 25.65 | 28.65 |
| 0215 x 028 | 1.03031 | 10.97 | 12.97 | 13.97 | 15.97 | 20.97 | 23.97 | 25.97 | 28.97 |
| 021 x 025 | 2.3323 | 9.67 | 11.67 | 12.67 | 14.67 | 19.67 | 22.67 | 24.67 | 27.67 |
| 021 x 028 | 2.0749 | 9.93 | 11.93 | 12.93 | 14.93 | 19.93 | 22.93 | 24.93 | 27.93 |

ACTUAL TORQUE FORCES

FIG. 16b

| U CENTRAL | TORQUE + 7 | TORQUE + 14 | TORQUE + 17 | TORQUE + 22 | TORQUE + 22 | TORQUE + 12 | TORQUE + 17 |
|---|---|---|---|---|---|---|---|
| SLOT SIZE | 0.022 | 0.018 | 0.018 | 0.018 | 0.018 | 0.022 | 20 SLOT |
| TECHNIQUE | ANDREWS | ALEXANDER | BENCH | HILGERS | RICKETTS | ROTH | HYBRID |
|  |  | 0 |  |  |  | 0 | 0 |
| 0 | ▓ |  |  |  |  | ▓ | ▓ |
| 1 | ▓ |  |  |  |  | ▓ | ▓ |
| 2 | ▓ |  |  |  |  | ▓ | ▓ |
| 3 | ▓ |  |  |  |  | ▓ | ▓ |
| 4 | ▓ |  |  |  |  | ▓ | ▓ |
| 5 | + 4.67 | + 6.3 |  |  |  | ▓ | ▓ |
| 6 |  | ▓ |  |  |  | ▓ | ▓ |
| 7 |  | ▓ |  |  |  | ▓ | ▓ |
| 8 |  | ▓ | + 9.3 |  |  | ▓ | ▓ |
| 9 |  | ▓ | ▓ |  |  | ▓ | ▓ |
| 10 |  | ▓ | ▓ |  |  | + 9.67 | ▓ |
| 11 |  | ▓ | ▓ |  |  |  | ▓ |
| 12 |  | + 11.67 | ▓ |  |  |  | ▓ |
| 13 |  |  | ▓ | + 14.3 | + 14.3 |  | ▓ |
| 14 |  |  | ▓ | ▓ | ▓ |  | ▓ |
| 15 |  |  | + 14.67 | ▓ | ▓ |  | + 14.67 |
| 16 |  |  |  | ▓ | ▓ |  |  |
| 17 |  |  |  | ▓ | ▓ |  |  |
| 18 |  |  |  | ▓ | ▓ |  |  |
| 19 |  |  |  | ▓ | ▓ |  | ▓ |
| 20 |  |  |  | + 19.67 | + 19.67 |  | + 19.9 |
| 21 |  |  |  |  |  |  |  |
| 22 |  |  |  |  |  |  |  |

* THE 19.9 TORQUE FOR THE HYBRID REPRESENTS THE PREFORMED AND PRETORQUE (6 DEGREES) UTILITY ARCH

FIG. 17

| U LATERAL | TORQUE + 3 | TORQUE + 7 | TORQUE + 10 | TORQUE + 14 | TORQUE + 14 | TORQUE + 8 | TORQUE + 12 |
|---|---|---|---|---|---|---|---|
| SLOT SIZE | 0.022 | 0.018 | 0.018 | 0.018 | 0.018 | 0.022 | 20 SLOT |
| TECHNIQUE | ANDREWS | ALEXANDER | BENCH | HILGERS | RICKETTS | ROTH | HYBRID |
|  | 0 | 0 |  |  |  | 0 | 0 |
| 0 | ▓ |  |  |  |  | ▓ | ▓ |
| 1 | + 0.67 | ▓ | + 2.3 |  |  | ▓ | ▓ |
| 2 |  | ▓ | ▓ |  |  | ▓ | ▓ |
| 3 |  | ▓ | ▓ |  |  | ▓ | ▓ |
| 4 |  | ▓ | ▓ |  |  | ▓ | ▓ |
| 5 |  | + 4.67 | ▓ | + 6.3 | + 6.3 | ▓ | ▓ |
| 6 |  |  | ▓ | ▓ | ▓ | + 5.67 | ▓ |
| 7 |  |  | ▓ | ▓ | ▓ |  | ▓ |
| 8 |  |  | + 7.67 | ▓ | ▓ |  | ▓ |
| 9 |  |  |  | ▓ | ▓ |  | ▓ |
| 10 |  |  |  | ▓ | ▓ |  | + 9.67 |
| 11 |  |  |  | ▓ | ▓ |  |  |
| 12 |  |  |  | + 11.67 | + 11.67 |  |  |
| 13 |  |  |  |  |  |  |  |
| 14 |  |  |  |  |  |  | ▓ |
| 15 |  |  |  |  |  |  | + 14.9 |

* THE 19.9 TORQUE FOR THE HYBRID REPRESENTS THE PREFORMED AND PRETORQUE (6 DEGREES) UTILITY ARCH

FIG. 18

| U CUSPIDS | TORQUE −7 | TORQUE −3 | TORQUE +7 | TORQUE +7 | TORQUE +7 | TORQUE −2 | AND +7/−7 |
|---|---|---|---|---|---|---|---|
| SLOT SIZE | 0.022 | 0.018 | 0.018 | 0.018 | 0.018 | 0.022 | 20 SLOT |
| TECHNIQUE | ANDREWS | ALEXANDER | BENCH | HILGERS | RICKETTS | ROTH | HYBRID |
| −7 | | | | | | | |
| −6 | −4.67 | | | | | | |
| −5 | | | | | | | −4.67 |
| −4 | | | | | | | |
| −3 | | | | | | | |
| −2 | | 0.67 | | | | | |
| −1 | | | 0 | 0 | 0 | | |
| 0 | 0 | 0 | | | | 0 | |
| 1 | | | | | | | |
| 2 | | | | | | | |
| 3 | | | | | | | |
| 4 | | | | | | | |
| 5 | | | 4.67 | 4.67 | 4.67 | | 4.67 |
| 6 | | | | | | | |
| 7 | | | | | | | |

THE POSITIVE AND NEGATIVE TORQUES ARE ACHIEVED BY REVERSING THE CUSPID BRACKET ON THE SAME CROWN

FIG. 19

| U BICUSPIDS | TORQUE −7 | TORQUE −7 | TORQUE −7 | TORQUE −7 | TORQUE 0 | TORQUE −7 | TORQUE −7 AND −11 |
|---|---|---|---|---|---|---|---|
| SLOT SIZE | 0.022 | 0.018 | 0.018 | 0.018 | 0.018 | 0.022 | 20 SLOT |
| TECHNIQUE | ANDREWS | ALEXANDER | BENCH | HILGERS | RICKETTS | ROTH | HYBRID |
| −11 | | | | | | | |
| −10 | | | | | | | −8.67 |
| −9 | | | | | | | |
| −8 | | | | | | | |
| −7 | | | | | | | |
| −6 | −4.67 | −4.67 | −4.67 | −4.67 | | −4.67 | −4.67 |
| −5 | | | | | | | |
| −4 | | | | | | | |
| −3 | | | | | | | |
| −2 | | | | | | | |
| −1 | | | | | | | |
| 0 | 0 | 0 | 0 | 0 | 0 | 0 | 0 |

FIG. 20

| L ANTERIORS | TORQUE −1 | TORQUE −5 | TORQUE −1 | TORQUE −1 | TORQUE 0 | TORQUE −1 | TORQUE 0 |
|---|---|---|---|---|---|---|---|
| SLOT SIZE | 0.022 | 0.018 | 0.018 | 0.018 | 0.018 | 0.022 | 20 SLOT |
| TECHNIQUE | ANDREWS | ALEXANDER | BENCH | HILGERS | RICKETTS | ROTH | HYBRID |
| −5 | | | | | | | |
| −4 | | 2.67 | | | | | 2.9 |
| −3 | | | | | | | |
| −2 | | | | | | | |
| −1 | | | | | | | |
| 0 | 0 | 0 | 0 | 0 | 0 | 0 | 0 |

THE 2.9 DEGREE TORQUE ON THE HYBRID REPRESENTS THE ADDITION OF THE 0.19 X 0.19 PRETORQUED (6 DEGREES) AND PREFORMED ADJUSTABLE UTILITY ARCH SEGMENT USED AS AN OVERLAY WITH A .030 BRACKET SLOT

FIG. 21

| L CUSPIDS | TORQUE −11 | TORQUE −7 | TORQUE +7 | TORQUE +7 | TORQUE +7 | TORQUE −11 | TORQUE −11 AND +7/−7 |
|---|---|---|---|---|---|---|---|
| SLOT SIZE | 0.022 | 0.018 | 0.018 | 0.018 | 0.018 | 0.022 | 20 SLOT |
| TECHNIQUE | ANDREWS | ALEXANDER | BENCH | HILGERS | RICKETTS | ROTH | HYBRID |
| −11 | | | | | | | |
| −10 | −8.67 | | | | | −8.67 | −8.67 |
| −9 | | | | | | | |
| −8 | | | | | | | |
| −7 | | | | | | | |
| −6 | | | | | | | |
| −5 | | −4.67 | | | | | −4.67 |
| −4 | | | | | | | |
| −3 | | | | | | | |
| −2 | | | | | | | |
| −1 | | | 0 | 0 | 0 | | |
| 0 | 0 | 0 | | | | 0 | |
| 1 | | | | | | | |
| 2 | | | | | | | |
| 3 | | | | | | | |
| 4 | | | | | | | |
| 5 | | | 4.67 | 4.67 | 4.67 | | 4.67 |
| 6 | | | | | | | |
| 7 | | | | | | | |

THE VARIETY OF TORQUES EXPRESSED WITH THE HYBRID SYSTEM REFLECTS THE REVERSIBILITY OF THE +7/−7 CUSPID BRACKET, ALONG WITH THE −11 TORQUE EXTRACTION-TYPE BRACKET

FIG. 22

| L FIRST BI | TORQUE −17 | TORQUE −11 | TORQUE −11 | TORQUE −11 | TORQUE 0 | TORQUE −17 | TORQUE −11 AND −17 |
|---|---|---|---|---|---|---|---|
| SLOT SIZE | 0.022 | 0.018 | 0.018 | 0.018 | 0.018 | 0.018 | 20 SLOT |
| TECHNIQUE | ANDREWS | ALEXANDER | BENCH | HILGERS | RICKETTS | ROTH | HYBRID |
| −17 | | | | | | | |
| −16 | −14.67 | | | | | −14.67 | −14.67 |
| −15 | | | | | | | |
| −14 | | | | | | | |
| −13 | | | | | | | |
| −12 | | | | | | | |
| −11 | | | | | | | |
| −10 | | −8.67 | −8.67 | −8.67 | | | −8.67 |
| −9 | | | | | | | |
| −8 | | | | | | | |
| −7 | | | | | | | |
| −6 | | | | | | | |
| −5 | | | | | | | |
| −4 | | | | | | | |
| −3 | | 3.3 | 3.3 | 3.3 | | | |
| −2 | | | | | | | |
| −1 | | | | | | | |
| 0 | 0 | | | | 0 | 0 | 0 |

FIG. 23

| L SECOND BI | TORQUE – 22 | TORQUE – 17 | TORQUE – 22 | TORQUE – 17 | TORQUE – 14 | TORQUE – 22 | TORQUE – 17 AND – 22 |
|---|---|---|---|---|---|---|---|
| SLOT SIZE | 0.022 | 0.022 | 0.022 | 0.018 | 0.018 | 0.022 | 20 SLOT |
| TECHNIQUE | ANDREWS | ALEXANDER | BENCH | HILGERS | RICKETTS | ROTH | HYBRID |
| –22 | | | | | | | |
| –21 | –19.67 | | –19.67 | | | –19.67 | –19.67 |
| –20 | | | | | | | |
| –19 | | | | | | | |
| –18 | | | | | | | |
| –17 | | | | | | | |
| –16 | | –14.67 | | –14.67 | | | –14.67 |
| –15 | | | | | | | |
| –14 | | | –14.3 | | | | |
| –13 | | | | | –11.67 | | |
| –12 | | | | | | | |
| –11 | | | | | | | |
| –10 | | | | | | | |
| –9 | | –9.3 | | –9.3 | | | |
| –8 | | | | | | | |
| –7 | | | | | | | |
| –6 | | | | | –6.3 | | |
| –5 | | | | | | | |
| –4 | | | | | | | |
| –3 | | | | | | | |
| –2 | | | | | | | |
| –1 | | | | | | | |
| 0 | 0 | 0 | 0 | 0 | 0 | 0 | 0 |

FIG. 24

HYBRID ORTHODONTIC BRACKET SYSTEM AND METHOD

BACKGROUND AND SUMMARY OF THE INVENTION

The present invention relates to a hybrid orthodontic bracket system and method. More particularly, the present invention relates to an apparatus and method for improving orthodontic bracket and archwire techniques by combining the capabilities of most current and popular edgewise appliance (bracket) designs and corresponding methods and techniques into a single appliance system. This is achieved by cutting, casting, molding, or by other methods of manufacturing bracket slots, stems and/or bases with the appropriate torquing angles, tipping angles, in-out compensations, rotational adjustments and slot dimensions to be used in conjunction with various types and diameters of archwires which will require little or no bending by the operator. The aforementioned preadjustments built into the bracket system, which is directly bonded or banded to the crowns, will, when combined with the force and resiliency of a preformed archwire, direct the crowns into predetermined positions which will represent the various methods and techniques of most current and popular techniques practiced by individual operators.

Early edgewise appliances incorporated very few or no built-in preadjustments and required that crown movement be achieved by placing complex bends into archwires by individual practitioners. The term "edgewise" refers to an orthodontic bracket with a rectangular archwire slot designed so that a square or rectangular archwire has to be inserted with its long dimension placed horizontally into the bracket slot. This "wire bending" procedure led to difficulty in treatment, particularly in the areas of time expended per patient and in the reproducibility of results. In response to these difficulties along with the inconsistencies he observed in treatment results among his peers, Dr. Lawrence Andrews developed the first fully preadjusted and integrated appliance system based upon the crown and occlusal relationships of 120 non-orthodontically treated "normal" dentitions. Preadjusted systems essentially have all necessary angles and planes of movement manufactured directly into the bracket which, when properly placed on the crown, eliminates or greatly reduces the need for wire bending by the operator to achieve desired crown movements. These angles are commonly referred to as "tip", "torque", "in-out" and "anti-rotation." These so-called "straight-wire" appliances would, in effect, allow the memory of unbent archwires to work with the preadjustments to guide teeth into ideal positions. Tremendous professional acceptance and commercial success of the straight-wire appliance led to the development and manufacture of various competitive bracket system designs. All these designs propose various treatment techniques, methods, or philosophies that distinguish systems from one another, particularly in the preferred torque preadjustments.

As more clinicians and manufacturers became involved in the use and design of preadjusted bracket systems, various new techniques and systems were developed. These developments were expressed in appliance design by the selection of various torques, tips, in-outs and anti-rotations that varied from the original Andrews designs. These new designs are essentially various methods for achieving largely uniform and agreed upon goals, best outlined in Dr. Andrews article "The Six Keys to Normal Occlusion." These general goals are proper molar relationships, crown angulations (tip) and crown inclinations, absence of rotations, tight contacts between teeth and a level or slight curve of Spee. For example, Dr. Ronald Roth, while expressing support for Andrews' conclusions, nonetheless determined that overcorrection in most places of movement is the best method for achieving these goals and subsequently designed a "straight-wire" appliance containing these overcorrections. Differences between systems are generally highlighted to promote an exclusivity of design allowing for claims of a proprietary edge in the marketplace. Closer examination shows that the differences between various systems in many preadjustments is not substantial due to goal uniformity. Tip and in-out preadjustments have, in fact, become so uniform as to create little difference between systems. Torque, however, has remained highly variable between systems.

Currently, preadjusted appliance systems are largely technique specific and allow the operator little opportunity to practice techniques promoted by other, mostly nationally known, appliance developers. Differences between systems are usually highlighted by clinicians and manufacturers to promote an exclusivity of the technique and corresponding bracket system thus allowing for claims of a proprietary "edge" in the marketplace. As no single treatment method or system holds all the answers for each individual patient (as evidenced by all the various bracket systems and complimentary techniques), practitioners become "locked in" to a single or limited treatment philosophy. Patient needs can vary widely in individual practices. Specific appliance designs appear to work more efficiently in certain case types, while not as well in others. For example, Ricketts-type practitioners often find this appliance most effective for young children without full permanent dentition when practicing "two-by-four" therapy, while Roth-type practitioners can obtain Andrews ideal crown positions more easily with the common 0.019×0.025 rectangular finishing wire. Mixing competitive bracket systems and techniques within private practices is largely unknown and resisted by doctors and staff due to the difficulties in efficiently managing the variables this would present. In addition, several different types of bracket systems would have to be stored in inventory adding substantially to overhead cost.

An object of this invention is to offer an appliance system that combines the potential of all major systems into one "hybrid" appliance system. The hybrid bracket system of the present invention, then, is not a new technique but rather a slot design (as expressed in the brackets by selections of various tips, torques, in-out compensations, rotational compensations, and slot dimensions) that allows practicing most major orthodontic techniques with one appliance design. It is in this way that it has its greatest utility for the operator.

One advantage of the present invention is that nearly any orthodontic technique or mechanical sequence available or recommended from all currently available and popular bracket systems can be performed with the single hybrid bracket system.

Another advantage of the present invention is that the orthodontic procedures that are by far the most popular (Roth, Andrews, Alexander Mechanics) can be performed on less than full sized archwires while still delivering the necessary torques. Full size wires (equal in width to the slot width of the bracket) are often difficult to fit into bracket slots unless the slots are in perfect alignment. This is most often not the case due to limitations in human ability to visualize and place brackets so perfectly, along with variations in crown anatomy which makes this task further improbable or impossible. Most clinicioners, then, will not follow the mechanical sequence recommended by most developers due to the inability to "fill" the bracket slot with full size wires. Even if attempted, achieving the "ideal" or recommended finishing torque positions, as outlined by appliance developers, may be impossible given deviation angles necessary to place "full-size" wires into bracket slots. In other words, some "play" must be necessary just to insert the wire into the slot, leading to less than full expression of built-in torques. Andrews, in fact, recommends against the use of full-sized rectangular finishing wires, which is surprising given his stated goals but understandable given the difficulties in doing so. Wire "rounding" due to the inability to manufacture perfectly square or rectangular archwires also dramatically reduces the actual torque delivered, further reducing the ability to reach stated torquing goals. The use of full size wires is not generally necessary with the hybrid bracket system to achieve "ideal" or recommended torques outlined by major clinicioners. Wire rounding effects may also be compensated for given the available option of selecting a larger finishing wire.

Still another advantage of the present invention is that the less than full sized wires will not express the leveling, tip, and axial (torque) positioning errors as dramatically as full sized wires. Extensive and varied published data, in fact, often recommends against filling the bracket slot in order to avoid the unintended effects of clinically expressing the errors in placement.

Still another advantage, less than full sized wires can deliver less overall force, due to smaller diameters and heightened torque built into the appliance, and can thus be introduced earlier in treatment with lesser fears of damage to the dentition and root structure while providing the same levels of torque correction.

A further advantage of the present invention is that a 0.016×0.016 wire (generally considered the smallest potential edgewise starting or finishing wire) will be at the passive borderline of the torque range in the hybrid bracket system. No correction will be delivered, but the bracket and crown will also not be allowed to "drift" excessively into an undesirable position before slot/wire "binding" takes place. In some known techniques and bracket systems, the 0.016× 0.016 wire will deliver high amounts of torque, while in other systems, this wire will fit so loosely in the slot as to allow much wire "play" and potential for crown drifting. This 0.016×0.016 wire is the beginning point in the hybrid system at which torque delivered can steadily and incrementally rise up to full or desired expression.

Most competitive orthodontic appliance systems allow for positive or negative torque cuspids, but not both. The torque choice reflects a treatment philosophy that is quite specific, and would not allow for crossover among or between systems. The hybrid bracket system of the present invention allows an operator a choice between either positive or negative torque cuspids, dependent on patient considerations.

Various torque choices are also available for the bicuspid brackets, which would depend on the actual torque the operator wishes to express along with archwire choice. For example, current 0.022 Roth systems with a popular 0.018× 0.025 finishing wire choice would deliver no torque in the upper bicuspids. The hybrid bracket system of the present invention offers the same torquing choice in the anterior segment (on smaller wires) and allows the doctor to add bicuspid torque by substituting the more common −7° torque bracket with the hybrid −11° torque bracket. Bicuspids are reversible between arches, and a vertical slot is built in to accommodate hooks for elastics.

The hybrid bracket system of the present invention advantageously provides a distinct upper and lower cuspid bracket for bicuspid extraction cases. Most competitive systems demand that extraction and non-extraction procedures, which vary dramatically in mechanical considerations, be done on the same type of cuspid brackets. To enhance the mechanical demands of retracting the cuspids into open bicuspid extraction sites, tip is increased, torque is lessened and anti-rotation added. A vertical bracket slot is added to allow insertion of a specifically designed hook for attaching elastics.

An additional advantage is that, for all the versatility provided by the system, only seventeen brackets need be manufactured or inventoried to obtain all the capabilities outlined. This number of brackets is comparable or less than other, less versatile, systems. For example, the "A" Company Roth Mini-Twin appliance requires 18 individual brackets and does not include a separate extraction-series bracket for the cuspids.

Creating a bracket system that combines the abilities of most known appliance systems into one hybrid appliance appears to be impossible with the highly variable nature of torque preadjustments between systems. Tip, in-out and anti-rotation, however, are generally expressed uniformly no matter what slot or archwire is employed, and these angles are largely uniform and agreed upon. For example, a 5 degree tip angle placed in a bracket will be expressed evenly no matter if the bracket is an 0.018 or 0.022 slot and generally with little regard to the size or type (round or rectangular) of archwire used. With torque, two other variables will greatly determine how the "built in" preadjustment will perform. These variables include the archwire size and the slot diameter. These two variables combine to determine actual torque values. For example, a +12 torque preadjusted bracket with an 0.022 slot and a 0.019×0.025 archwire will create an actual torque of only +4.75°. Changing the slot to an 0.018 width and placing a 0.016× 0.022 wire in the +12° preadjusted bracket slot creates an actual torque of +6.60°. So, when it comes to the torque component, whatever is built in is modified by the combination of slot diameter and size of the selected archwire. Wire is an important variable, as doctors have access to a large variety of square and rectangular archwires. Built-in torque and slot choice is ultimately more important as they dictate the available range of axial movement (torque). Brackets also cannot be changed or substituted nearly as easily or cost effectively as may archwires.

As discussed above, the bracket system of the present invention allows for most popular, currently available torques to be expressed in one hybrid appliance design when matched with the appropriate square or rectangular archwires. This, in combination with the other currently accepted and largely uniform tips, in-outs and anti-rotations, allows substantially all known methods and techniques to be practiced on one appliance. (It should be noted that no clinician expects the tips, torques, and in-outs to be perfectly identical to any competitive design. Preadjusted systems, as discussed, are by nature not exacting as they are based on averages of non-orthodontic normals. Two degree variances are considered well within the acceptable range.)

In the present invention, instead of a conventional 0.018 or 0.022 bracket slot width, the hybrid bracket system incorporates an 0.020 bracket slot width into each bracket. Various torques can be systematically created for each individual bracket that can replicate any existing system through the choice of the appropriate archwire, while maintaining an integrated "straight-wire" philosophy. The range of available torques in this system, then, would be a key to its flexibility and would separate it from any other commercially available bracket system. The commonly employed tips, in-outs and anti-rotation would also be combined with these torque preadjustments.

The upper and lower non-extraction cuspid brackets are designed to be reversible without affecting angulation but reversing the torque. Some bracket systems call for either positive or negative torque on the cuspids, and this reversibility without affecting angulation or in-out maintains the all encompassing nature of this appliance. A vertically slotted bracket would allow for the insertion of a hook device for attaching elastics after the choice of a positive or negative torque has been made. Proportionality in and between systems can be maintained or enhanced with the hybrid through proper bracket choice. This concept relates to the amount of torque variance between central and cuspid brackets. For example, although the Hilgers/Ricketts formulas are substantially different in torque generation from the Andrews prescription, they contain 16° and 15° torque differential central to cuspid, respectively, which is highly uniform.

An accurate and detailed analysis of actually expressed torques is provided with this system. This is not available in any other systems, largely due to their technique sensitive nature. Many operators of competitive systems are assumed to be expressing the full built-in torques, or are following a highly uniform mechanic sequence to obtain uniformity of results.

In order for brackets with preadjustments to work in union and harmony with one another, bracket placement must be accurate and precise, not only for individual brackets on crowns, but relative to one another. It is known and documented that placing brackets higher or lower vertically on crowns will affect actual torque generation. If placed higher or lower uniformly bracket to bracket, this phenomenon can be more easily managed. If brackets, however, are placed higher or lower relative to one another, the built-in preadjustments, designed to be systematic and interrelated, begin working in disharmony.

To facilitate proper placement and expression of bracket torques relative to one another, the system should include a mesial-distal (horizontal) line etched, painted, cast, molded or otherwise on the bracket or bonding pad or welding flange to determine the "coplanar" level slot lineup. Due to the angled torque preadjustments, the slot opening at the bracket face point often gives a misleading impression of level slot lineup, as the slot bottom (hidden from clear view) may lie on a different plane. The line on the bracket, flange or pad should identify the slot base point, represented by the horizontal line, thus allowing for slot base points to be accurately aligned verses the more inaccurate slot face points. This can be joined with the more common long axis bracket/pad lines (designed to correctly express tip preadjustments) to create a "crosshair" effect, thus heightening the ability to correctly place, and correctly express, built-in bracket preadjustments.

This hybrid orthodontic bracket system of the present invention is not a new technique, but rather a vehicle for incorporating substantially all known orthodontic techniques into one appliance design. It is in this way that it has its greatest utility for the operator.

According to one aspect of the present invention, an orthodontic bracket system includes a plurality of rectangular wires having a plurality of different sizes, and a plurality of brackets including an upper bicuspid bracket, an upper cuspid bracket, an upper lateral bracket, an upper central bracket, a lower bicuspid bracket, a lower cuspid bracket, and a lower anterior bracket. Each of the plurality of brackets is formed to include a 0.020 inch slot for receiving a selected one of the plurality of rectangular wires therein. The slots are aligned at predetermined torque angles to facilitate the practice of nearly any orthodontic technique or mechanical sequence available or recommended from all currently available and popular bracket systems on the hybrid bracket system of the present invention.

In the illustrated embodiment, the upper central bracket includes means for applying any actual torque force to an upper central tooth in a range of actual torque forces from about 0° to above +10° to an upper central tooth. The upper lateral bracket includes means for applying any actual torque force to an upper lateral tooth in a range of actual torque forces from about 0° to above +6° to an upper lateral tooth. The upper cuspid bracket includes means for applying any actual torque force to an upper cuspid tooth in a range of actual torque forces from above −4° to above +4° to an upper cuspid tooth. The upper bicuspid bracket includes means for applying any actual torque force to an upper bicuspid tooth in a range of actual torque forces from about 0° to below −5°.

Additional objects, features, and advantages of the invention will become apparent to those skilled in the art upon consideration of the following detailed description of a preferred embodiment exemplifying the best mode of carrying out the invention as presently perceived. For example, individual operators have a defined and verifiable method for creating their own specific technique or system that falls in the intermediate ranges of torque available, which can vary patient to patient depending on individual case types and requirements. It should be noted that there is no officially sanctioned or preferred method for treating cases orthodontically.

BRIEF DESCRIPTION OF THE DRAWINGS

The detailed description particularly refers to the accompanying figures in which:

FIG. 5a is a chart illustrating torque angles preformed into various available conventional bracket systems.

FIG. 5b is a chart illustrating angulations preformed into various available conventional bracket systems.

FIG. 8 is a chart illustrating the preset torque angles, angulation angles, anti-rotation and in-out features of the hybrid bracket system of the present invention.

FIG. 9 is a chart illustrating features of additional brackets in an optional extraction bracket series of the hybrid bracket system of the present invention.

FIGS. 12 and 13 provide a comparison between a standard bracket illustrated in FIG. 12 and a rhomboidal bracket illustrated in FIG. 13. In FIGS. 12 and 13, the bracket face is formed to include a slot having a predetermined tip angulation to adjust a tip of the tooth when the bracket is aligned on the crown's long axes and a wire is inserted into the slot. The facial configuration is commonly termed "rhomboidal." Both angulated slots and angulated bracket braces will work equally as well when correctly placed, but it is commonly assumed that the rhomboidal designs are easier to place correctly.

FIG. 14 is a chart illustrating actual torque forces generated using a bracket having a 0.020 inch slot width with various sizes of square and rectangular wires, using the more common, but less reliable, assumptions of perfectly square or rectangular archwires and bracket slots.

FIG. 15 is a chart illustrating actual torque forces generated using a bracket having a 0.018 inch slot width formed with various sizes of rectangular and square wires.

FIG. 16 is a chart illustrating actual torque forces generated using a bracket having a 0.022 inch slot width with various sizes of rectangular and square wire sizes;

FIG. 17 is a chart illustrating a range of actual torque values which can be applied by an upper central bracket of the hybrid bracket system of the present invention compared to a range of actual torque values for upper central brackets for six conventional bracket systems. Other less popular systems generally have preadjustments identical or largely similar to the systems illustrated.

FIG. 18 is a chart illustrating a range of actual torque values which can be applied by an upper lateral bracket of the hybrid bracket system of the present invention compared to a range of actual torque values for upper lateral brackets for six conventional bracket systems.

FIG. 19 is a chart illustrating a range of actual torque values which can be applied by an upper cuspid bracket of the hybrid bracket system of the present invention compared to a range of actual torque values for upper cuspid brackets for six conventional bracket systems.

FIG. 20 is a chart illustrating a range of actual torque values which can be applied by upper bicuspid brackets of the hybrid bracket system of the present invention compared to a range of actual torque values for upper bicuspid brackets for six conventional bracket systems.

FIG. 21 is a chart illustrating a range of actual torque values which can be applied by lower anterior brackets (central and lateral) of the hybrid bracket system of the present invention compared to a range of actual torque values for lower anterior brackets for six conventional bracket systems.

FIG. 22 is a chart illustrating a range of actual torque values which can be applied by lower cuspid brackets of the hybrid bracket system of the present invention compared to a range of actual torque values for lower cuspid brackets for six conventional bracket systems.

FIG. 23 is a chart illustrating a range of actual torque values which can be applied by lower first bicuspid brackets of the hybrid bracket system of the present invention compared to a range of actual torque values for lower first bicuspid brackets for six conventional bracket systems.

FIG. 24 is a chart illustrating a range of actual torque values which can be applied by lower second bicuspid brackets of the hybrid bracket system of the present invention compared to a range of actual torque values for lower second bicuspid brackets for six conventional bracket systems.

DETAILED DESCRIPTION OF THE DRAWINGS

Figure 1:
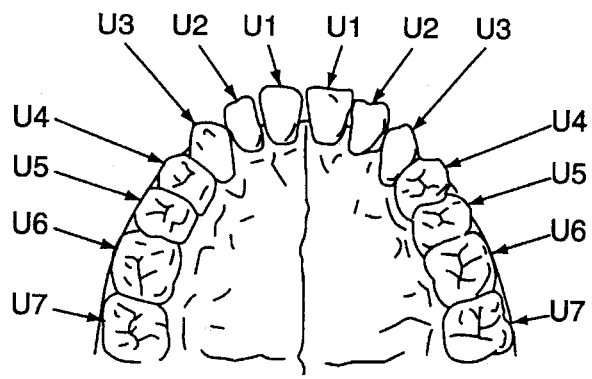
FIG. 1 is a plan view of a set of upper permanent teeth.

Referring now to the drawings, FIG. 1 illustrates a set of upper permanent teeth. Upper central teeth are labeled U1. Upper lateral teeth are labeled U2. Upper cuspids are labeled U3. Upper first bicuspids are labeled U4, and upper second bicuspids are labeled U5.

Figure 2:
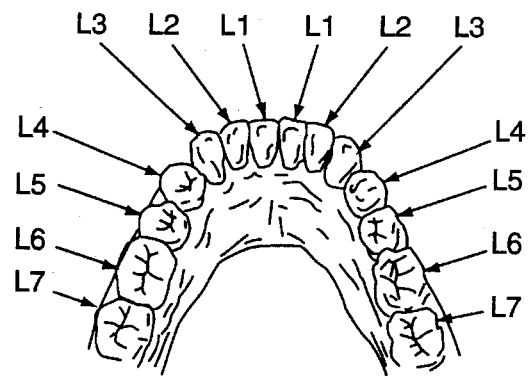
FIG. 2 is a plan view of a set of lower permanent teeth.

FIG. 2 illustrates a set of lower permanent teeth. Lower central teeth are labeled L1. Lower lateral teeth are labeled L2. Lower cuspids are labeled L3. Lower first bicuspids are labeled L4, and lower second bicuspids are labeled L5.

The present invention relates to a hybrid orthodontic bracket system and method for straightening upper and lower permanent teeth. Brackets can be applied to the teeth by banding or by gluing brackets with bonding bases directly to the teeth in conventional manners. The first orthodontic brackets did not incorporate any type of preadjustments in the brackets. Therefore, after the bracket was banded or bonded to a tooth, an orthodontist was required to bend archwires placed in the slot to control movement of the teeth. However, more modern bracket systems include brackets having slots aligned at angles and inclinations with varying base thicknesses and anti-rotations incorporated into the brackets to reduce greatly the need for bending wires.

First order bends are commonly referred to as "in-out" compensation. In-out adjustments are typically controlled by varying the thicknesses of bracket bases and stems. The in-out forces required to achieve normal crown positions for all teeth have been systematically quantified and built into the appliances. Although some exceptions have existed, uniform in-out compensations based on generally accepted normal crown positions are now accepted by nearly all clinicians and appliances. Therefore, only one type of first order bends are necessary for a hybrid appliance. Archwire adjustments are still often required to correct in-out adjustments with all systems. Therefore, the orthodontic bracket system of the present invention has adopted conventional in-out settings for the brackets.

Figure 3:
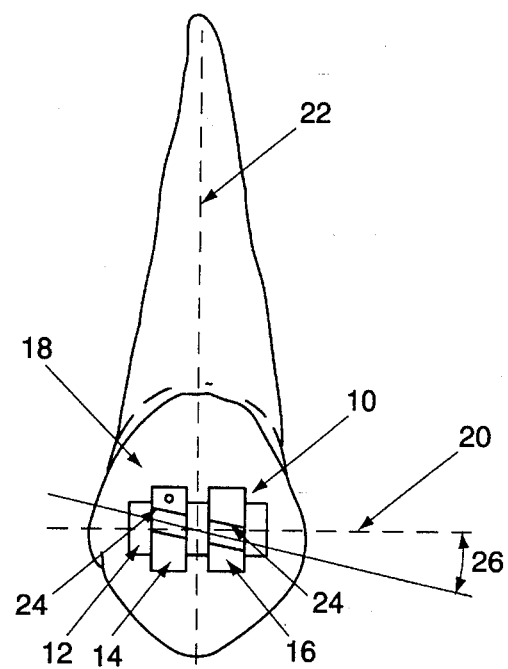
FIG. 3 is a diagrammatical illustration of an orthodontic bracket installed on a tooth, the bracket being formed to include a slot having a predetermined tip angulation to adjust a tip of the tooth when the bracket is aligned on the crowns long axis and a wire is inserted into the slot.

Second order bends are commonly referred to as "tip" or angulation. As illustrated in FIG. 3, a bracket 10 includes a base 12 and a pair of spaced-apart tie wings 14 and 16. Bracket 10 is mounted on a tooth 18 so that a horizontal axis 20 of base 12 is aligned perpendicularly to a longitudinal axis 22 of tooth 18. slot 24 is formed in each of tie wings 14 and 16 for receiving an archwire therein. In traditional bracket designs, as illustrated in FIG. 3, slot 24 is aligned at an angle relative to the horizontal axis 20 of base 12 as illustrated by angle 26. The angle 26 controls movement of the tip of tooth 18 upon insertion of a wire into slot 24. The new and more common rhomboidal designs achieve designated angulation by varying the bracket faces, with the advantage of easier overall placement.

Figure 6:
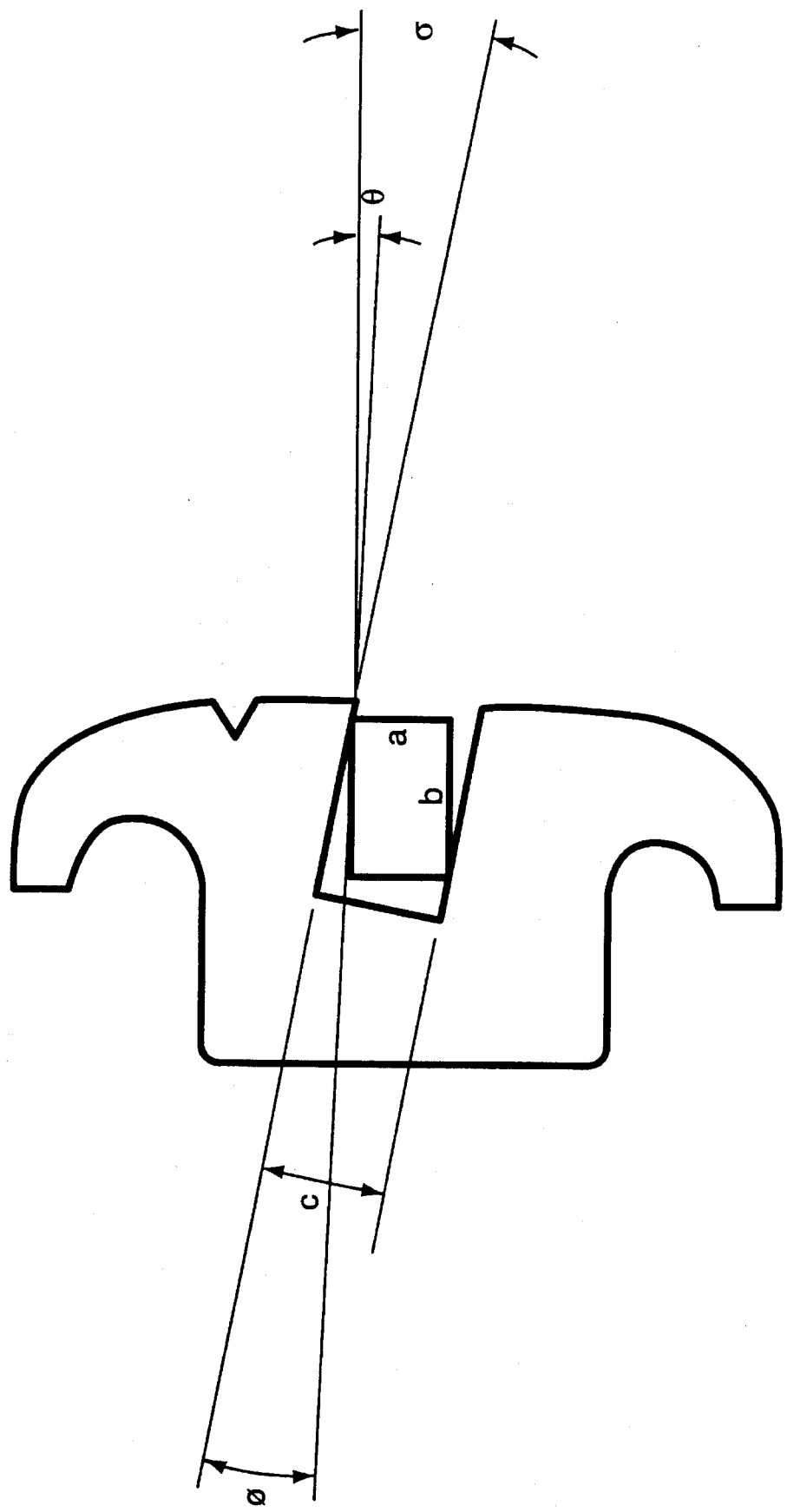
FIG. 6 is a diagrammatical view similar to FIG. 4 illustrating a plurality of variables used to calculate actual or effective torque values.

Several known bracket systems have been developed. The most common systems include Roth, Andrews, Wick, Hilgers, Bench, Ricketts, and Cetlin. A review of these systems indicates that tip angulation of the brackets in the various systems and techniques are strikingly similar and thus support the idea of uniform tip angulation values. As such, a hybrid bracket system with uniform second order bends becomes easily obtainable. The second order bend angulations of the bracket system of the present invention are illustrated in the chart of FIG. 6.

Figure 4:
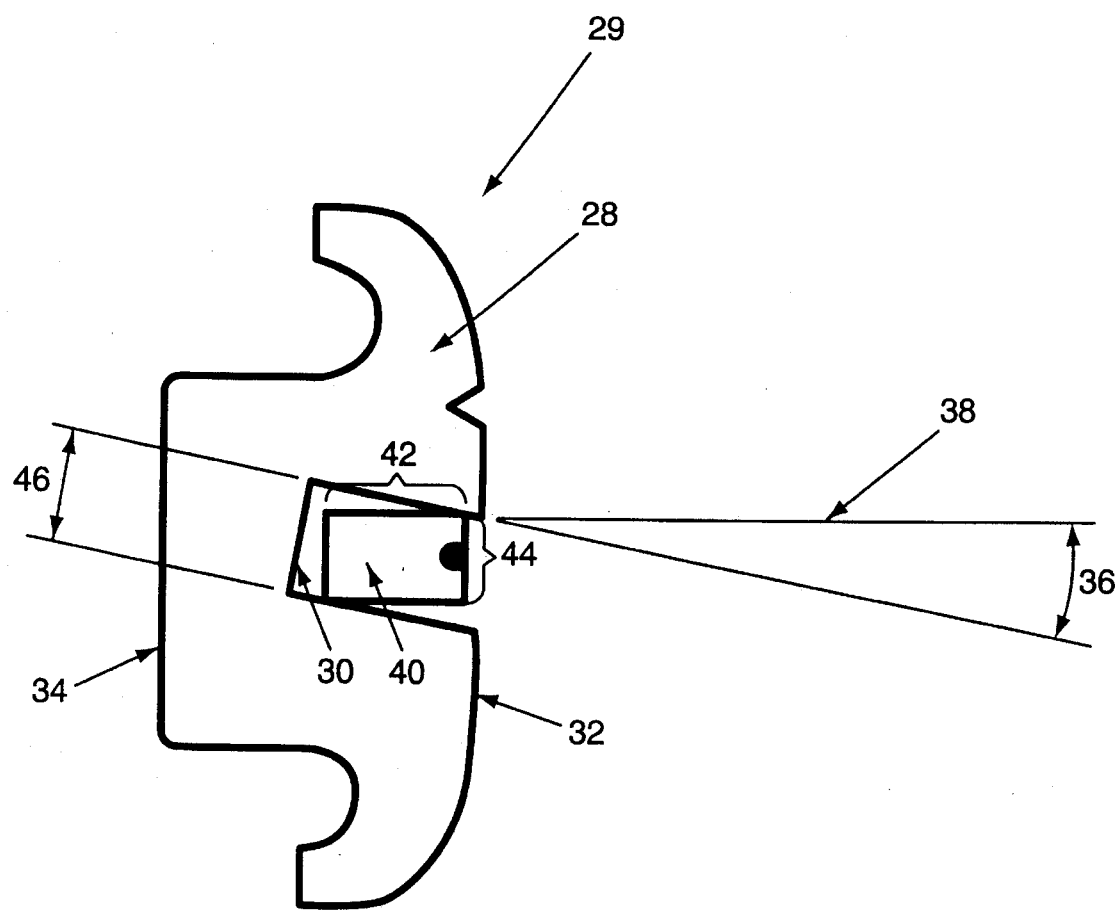
FIG. 4 is a diagrammatical view of an orthodontic bracket illustrating a slot aligned at a torque angle for generating torque forces on a tooth when the bracket is installed onto the tooth and a square or rectangularly-shaped straight wire is positioned in the slot.

The most important aspect of the present invention is related to third order bends. Third order bends are known as "torque". The application of torque forces is the point at which the known conventional systems vary widely. Torque inclination is illustrated in FIG. 4. Tie wings 28 of bracket 29 are formed to include a rectangularly shaped slot 30. Tie wings 28 include a front surface and a rear surface 34 for attaching to a bonding pad or band for bonding or banding to a tooth. Slot 30 is formed at an angle 36 relative to a line 38 perpendicular to front and rear surfaces 32 and 34. Angle 36 is known as the torque angle for bracket 29. Slot 30 is configured to receive a square or rectangularly-shaped wire 40 therein. The engagement between wire 40 and the side walls defining slot 30 applies a torque force to a tooth on which the bracket is mounted. Different torque angles 36 are typically formed into brackets for various teeth to apply different torque forces to each tooth.

As illustrated in the chart of FIG. 5a, a wide variety of torque angles are incorporated into known bracket systems. This variety of torque angles creates differences between the techniques practiced by orthodontists. The chart of FIG. 5b illustrates angulations for the various brackets systems disclosed in FIG. 5a. Another complete chart of various fixed appliance techniques is available on page 6 of the "Orthodontics" catalog available from Dentaurum, Inc. in Newtown, Pa. The wide range of built-in torque angles causes problems during an attempt to make a hybrid appliance. An object of the present invention is to incorporate torque angles 36 and slot widths 46 into brackets so that most conventional orthodontic techniques can be replicated using a single hybrid bracket system. Therefore, the practitioner does not have to stock a plurality of different bracket systems, one for each of the known techniques, or limit treatment options with a single appliance, which is more common.

An important consideration is not the torque angle built into the appliance but the actual torque forces generated when the slot width and wire dimensions are taken into consideration. The magnitude of the actual torque forces applied to the tooth is based upon the torque angle built into the bracket 36, the length 42, and width 44 of wire 40, and the width 46 of slot 30. These actual torque forces are determined by subtracting "slot play" or deviation angles in the bracket/wire combinations when using less than a full size square or rectangular archwire. FIG. 6 illustrates theoretical actual or effective torque values where:

φ=Deviation Angle

σ=Torque Angle
θ=Actual or Effective Torque Angle
a and b=wire dimensions
c=slot width To calculate the actual or effective torque values, the following equations are used:

$$\phi = \text{ARC SIN} \left[ \frac{bc - a\sqrt{a^2 + b^2 - c^2}}{a^2 + b^2} \right]$$

and $$\theta = \sigma - \phi$$

The more common "ideal" formulas, based on perfectly square or rectangular wire, have been supplemented with a more accurate formula which takes into consideration wire corner "rounding." The newer formula will proportionally alter all systems, thus no new torque preadjustments are necessary for the hybrid system.

Figure 7:
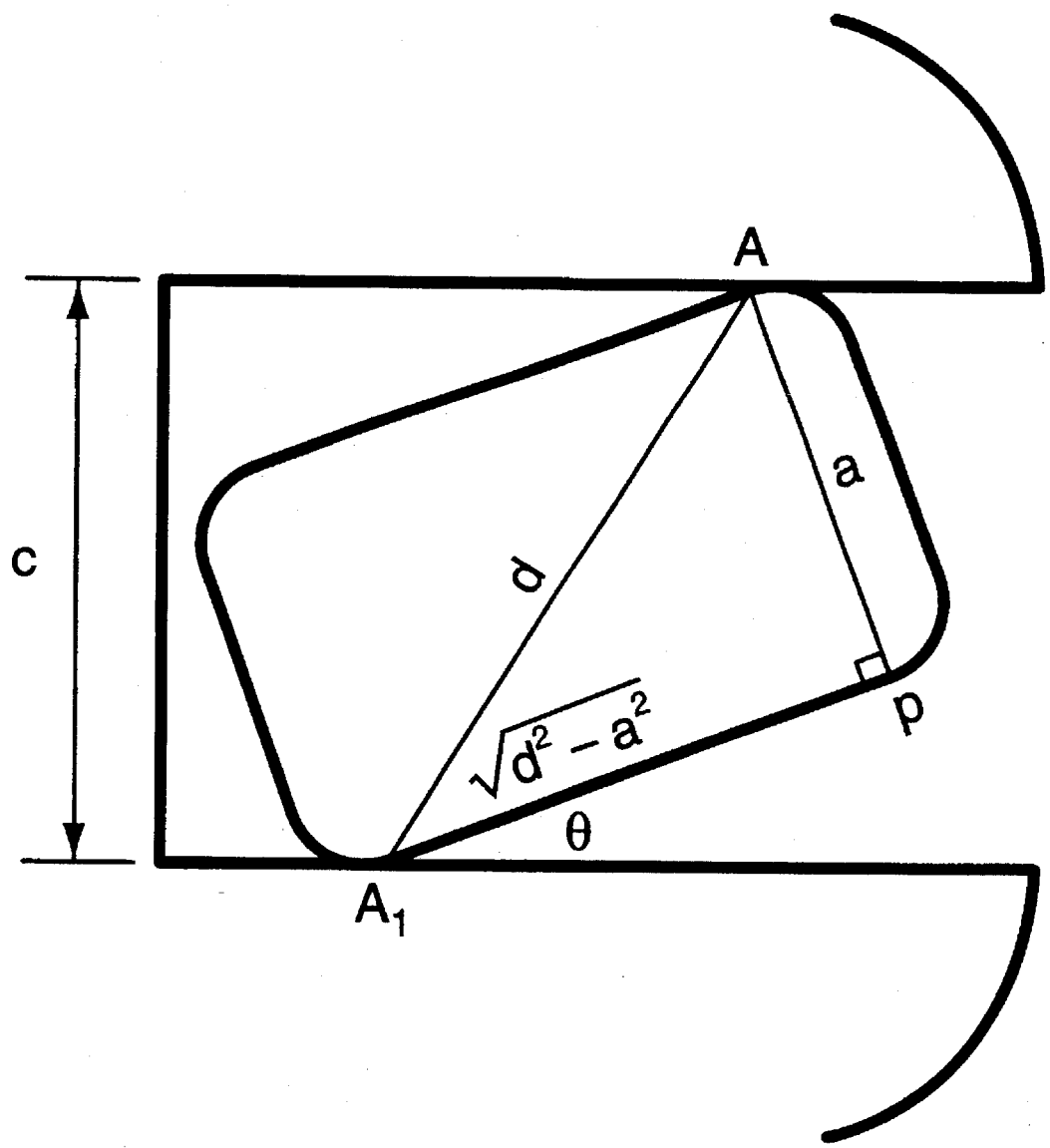
FIG. 7 is a diagrammatical view similar to FIG. 6 illustrating a plurality of variables used to calculate actual or effective torque values for a wire having bevelled edges.

An example of the updated method for calculating actual or effective torque forces is illustrated in FIG. 7. In this calculation, compensation is made for bevel edges on the rectangular wire. To calculate actual torque forces using a beveled wire the following equations are used with the values from FIG. 7:

$$\phi = \text{ARC SIN} \left[ \frac{c\sqrt{d^2 - a^2} - a\sqrt{d^2 - c^2}}{d^2} \right]$$

and $$\theta = \sigma - \phi$$

Low torque appliances are designed to move teeth only to ideal crown inclination, whereas high torque appliances are generally designed to overcorrect or overtreat, often in anticipation of relapse to the ideal positions. Given the much greater number and popularity of high torque appliances, most doctors in the United States would appear to typically finish cases in overcorrected or overtreated crown positions. In practice, however, there are three basic methods present when doctors choose finishing wires, and consequently actual torques. A minority of doctors will attempt a full torque expression in full-sized archwires. In other words, these doctors will select archwires having a width 44 substantially equal to the slot width 46. Another small number of orthodontists will finish with a round wire and therefore do not apply torque forces. A majority of orthodontists finish patient treatment with less than full size rectangular or square archwires. Therefore, when the orthodontist is using a high-torque appliance, he may in actuality not be overcorrecting due to a reduced size archwire.

Conventional systems use a 0.022 width slot or a 0.018 inch width slot. The hybrid bracket system of the present invention uses a 0.020 inch slot. By using the 0.020 inch slot, combined with bracket preadjustments and various sizes of wire, the hybrid bracket system of the present invention is able to generate a far wider range of torque forces than is available with any of the conventional bracket systems. Therefore, the hybrid bracket system of the present invention can be used to practice most of the known methods which, previously, would necessitate stocking several different types of bracket systems. The inventory of additional square or rectangular wires necessary to express a wide variety of torques would not be large and would be very inexpensive and easy to manage compared to inventorying numerous bracket systems.

Figure 11:
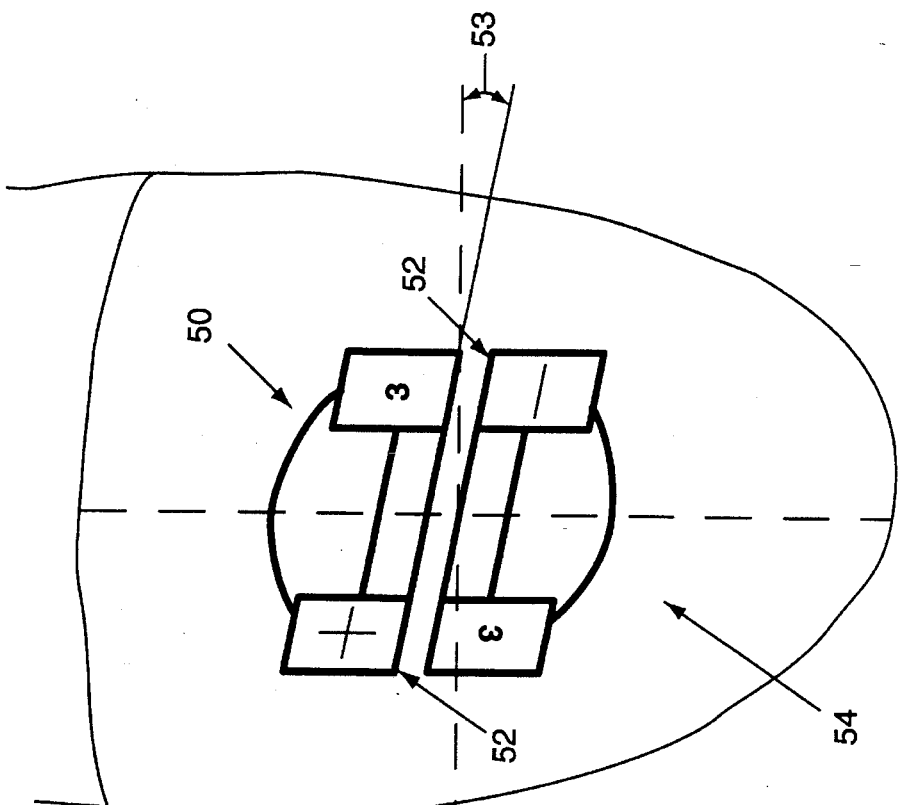
FIG. 11 is a diagrammatical view illustrating the bracket of FIG. 10 in a reversed orientation so that the slot is aligned at a +7° torque angle while maintaining the +10° angulation, due to the versatility of rounded base designs.
Figure 10:
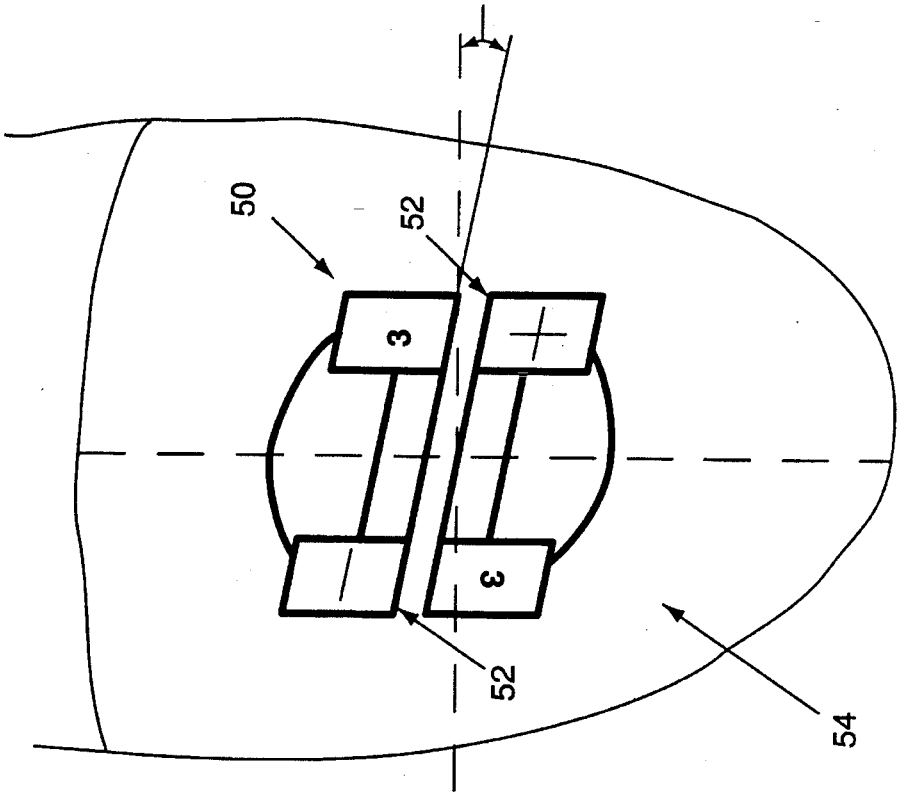
FIG. 10 is a diagrammatical view of a rhomboid-shaped cuspid bracket having a slot formed therein with a −7° torque angle and a +10° tip angulation.

The torque angles built into the brackets of the present invention are illustrated in FIG. 8. An optional extraction bracket series may also be provided. The torque, angulation, anti-rotation, in-out and ball hook notations for the extraction series bracket are illustrated in the chart of FIG. 9. In these instances, the upper and lower cuspid brackets are changed to the values illustrated in FIG. 9. All the brackets in the present invention include a 0.020 inch slot width. As illustrated in the chart of FIG. 8, the normal hybrid bracket system of the present invention includes upper central brackets (U1) having a +17° torque angle, an upper lateral (U2) bracket having a +12° torque angle. The hybrid bracket system of the present invention also includes upper and lower cuspid brackets (U3 and L3) which have either a +7° torque angle or a −7° torque angle. An advantage of the present invention is that a single upper cuspid bracket and a single lower cuspid bracket are provided to incorporate both the +7° torque angle and the −7° torque angle. This is accomplished by providing the rhomboidal bracket and rounded pad illustrated in FIGS. 10 and 11. In FIG. 10, the cuspid bracket 50 is positioned so that Slot 52 is aligned at a −7° torque angle. In other words, the slot 52 is higher near a front edge of bracket 50 than near a base of bracket 50. For example, the bracket of FIG. 4 mounted on an upper arch would create a positive torque, while the bracket of FIG. 4 mounted on a lower arch would create a negative torque. Slot 52 of bracket 50 is formed at a +10° angulation angle for providing tip movement of tooth 54. In FIG. 11, bracket 50 has been turned upside down on tooth 54. Because bracket 50 has the rounded pad, bracket 50 can be reversed, or turned upside down, the change the torque angle from −7° to +7°. In FIG. 11, slot 52 is lower adjacent to front edge of bracket 50 than at a back edge of bracket 50. Because of rounded pad of bracket 50, the bracket may be bonded in reverse position thus reversing torque and maintaining proper angulation, as illustrated by angle 53. FIG. 12 illustrates a standard rectangular bracket, and FIG. 13 illustrates a rhomboidal bracket. Either configuration can be used with the present invention.

The upper bicuspid brackets of the hybrid bracket system are formed to include a slot aligned at a −7° torque angle. An upper second bicuspid bracket is formed to include a slot aligned at a −11° torque angle. The lower central (L1) and lower lateral (L2) brackets are formed to include a slot having a 0° torque angle. The lower first bicuspid bracket is formed to include a slot aligned at a −17° torque angle. The hybrid bracket system also includes a second bicuspid (L5) bracket aligned at a −22° torque angle. All bicuspid brackets are interchangeable first to second, left to right, and upper to lower.

As discussed above, the actual torque forces which can be applied using a bracket system are different from the torque angles formed in the brackets. Wire size, built-in preadjustments, and slot width are all factors which control the actual torque values applied.

FIG. 14 is a chart illustrating actual torque forces generated using a 0.020 inch slot. The torque angle formed in the bracket is listed at the top of each column, and different rows illustrate various wire sizes which may be selected for use with the 0.020 slot. FIGS. 15 and 16 illustrate actual torque forces generated using a 0.018 width slot and/or a 0.022 inch width slot, respectively. As discussed above, conventional bracket systems use the 0.018 width slot and a 0.022 width slot. Using the tables of FIGS. 14–16, charts have been prepared for each bracket of the present invention to compare actual torque values applied by the bracket system of the present invention compared with known conventional brackets. Each chart represents the range of available actual torque values for each particular bracket. The smallest wire of presumed use is a 0.016 inch×0.016 inch square archwire. This is the smallest commonly employed edgewise wire. In 0.018 inch slot width bracket systems, the largest wire used presumed is a 0.017 inch×0.025 inch. In 0.022 slot bracket systems, the largest wire used presumed is 0.021 inch×0.025 inch archwire. These are generally the largest commonly employed edgewise wires in the respective slot choices. Any increase or decrease in actual torque ranges whether by wire choice or actual torque formula will proportionally alter all systems equally.

As illustrated in FIG. 17, the hybrid bracket of the present invention includes an upper central bracket (U1) which can apply a range of torque forces between 0 and +14.67°. The hybrid bracket can also apply a +19.9° torque using an adjustable preformed and pretorqued (6°) utility arch. It should be noted that using auxiliary sectional or utility arches in the high torque Ricketts and Hilgers systems is common practice and would not necessitate technique changes. The only difference is that torque is added to the auxiliary wire to enhance the operator's total torquing options. The preformed and adjustable nature of the arch, along with the use of nitinol-type wires adds greatly to ease of use, patient comfort, and predictability of results.

FIG. 17 also illustrates the range of actual torque values for six conventional bracket systems. An upper central bracket from an Andrews system can apply a range of torque values between 0° and +4.67° torque. An upper central bracket from an Alexander system can apply a range of torque forces between +6.3° and +11.67°. In upper central bracket from a Bench system can apply range of torque values between 9.3° and +14.67°. An upper central bracket from a Hilgers or Ricketts system can apply range or torque forces between +14.3° and +19.67°. An upper central bracket from a Roth system can apply range of torque values between 0° and +9.67°. It can be seen clearly in FIG. 13 that the hybrid bracket system of the present invention provides a wider range of available torque values along with the "passive border line" of torque which provides no correction in the smallest commonly used (0.016×0.016) edgewise wire, but largely disallows crown "drift" into undesirable positions. Therefore, the hybrid bracket system of the present invention is capable of practicing several known techniques using a single bracket system. For instance, if an orthodontist decides he wants to practice the Bench technique on one patient and a Roth technique on another patient, the orthodontist would normally have to stock both types of appliances. However, with the hybrid bracket system of the present invention, both the Bench method and the Roth method can be used with the single hybrid bracket system.

The range of actual torque forces in the commonly recognized "full-size" wire of an upper lateral bracket (U2) is from 0° to +9.67° as illustrated in FIG. 18. A +14.9° torque may be provided using the preformed and pretorqued 6° utility arch.

FIG. 19 illustrates the range of actual torque values which can be applied using an upper non-extraction cuspid bracket (U3) of the present invention. Because the bracket is reversible, a single upper cuspid bracket can apply an actual range of torque values from −4.67° to +4.67°.

For upper bicuspids, the normal bracket (U4) having a slot angle of −7° can apply a range of actual torque forces from 0° to −4.67° as illustrated in FIG. 20. A second bicuspid bracket having a slot angle of −11° can apply a range of actual torque values from 0 to −8.67°.

FIG. 21 illustrates the range of actual torque values for lower anterior brackets (L1 and L2). A −2.9° torque on the hybrid brackets represents the addition of the 0.019×0.019 pretorqued 6 degree and preformed adjustable utility arch segment used as an overlay with a 0.030 bracket slot.

The use of a pretorqued, adjustable utility segment versus a −5° anterior bracket in the Alexander system provides the operator with numerous advantages.

No torque need be generated in the posterior segments until desired.

No separate (0 torque) brackets are needed for cases that do not need anterior uprighting.

Tipback bends can be placed in the utility arches to facilitate molar uprighting.

A 0.017×0.025 lower finishing wire in the hybrid, which generates the full arch actual torques recommended by Alexander, will not be able to detorque the −2.9 initially generated by the utility wires. Lower lingual retainers could even be placed prior to debracketing which would enhance lower stability.

A 0.019×0.019 square wire is inherently less stiff than a 0.017×0.025 archwire. Utility segments could also be manufactured with superelastic wires to reduce patient trauma.

Most importantly, rotations and other initial movements can be allowed to work out prior to placement of large, stiff rectangular wires, thus reducing the potential for root resorption or damage particularly in the posterior segment of the dentition.

The chart of FIG. 22 illustrates the range of actual torque values applied by the lower cuspid (L3). Using the normal +7° or −7° bracket, a range of actual torque values from +4.67° to −4.67° can be obtained. Using the extraction bracket series which includes a torque slot angle at −11°, the range of torque angles can be extended to −8.67°.

FIG. 23 illustrates a range of actual torque values for the hybrid bracket system of the first lower bicuspid (L4). The torque ranges are from 0 to −14.67°.

FIG. 24 illustrates a range of actual to values for the second lower bicuspid (L5) brackets of the hybrid bracket system. The range of actual torque values is from 0 to −19.67°.

A complimentary selection of first and second molar attachments (referred to a buccal tubes) are also available in the hybrid system. Doctors commonly choose from a variety of available tube configurations, including "triple," "double" and "single" attachments. All types may be offered in the hybrid concept, although the preferred embodiment will be an upper triple convertible (one main slot, one auxiliary slot and one headgear tube with a removable cap on the main slot) and a lower double convertible (one main slot, one auxiliary slot with a removable cap on the main slot) with each incorporating a permanent hook device. Also, a higher torque and anti-rotation type will be offered along with a lower torque and anti-rotation type to satisfy these two general treatment philosophies. The one common and proprietary element in the hybrid system will be the use of a 0.020 inch main first and second molar archwire slot to compliment the use of the hybrid bracket appliance. A detailed description of the preferred (lower torque) embodiment follows:

|  | TIP | IN-OUT | ANTI-ROTATION | MAIN SLOT |
|---|---|---|---|---|
| 1ST MOLAR TORQUE UPPER −11 | 0 | THIN | 12 DEGREES | .020 |
| 1ST MOLAR TORQUE UPPER −25 | 0 | THIN | 8 DEGREES | .020 |
| 2ND MOLAR TORQUE UPPER −11 | 0 | THIN | 12 DEGREES | .020 |
| 2ND MOLAR TORQUE UPPER −25 | 0 | THIN | 6 DEGREES | .020 |

Figure 25:
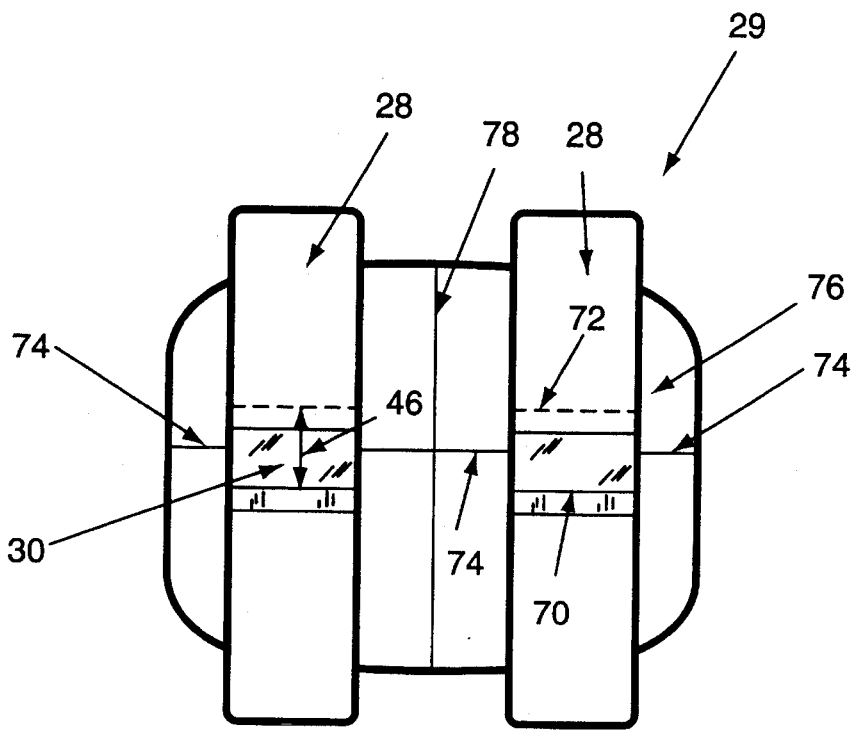
FIG. 25 is a diagrammatical front elevational view of the bracket of FIG. 4 illustrating a horizontal marking formed on a base of the bracket to provide an indication of the position of a true center line of the bottom surface of the slot relative to the front bracket face, thereby facilitating alignment of the bracket on the tooth.

FIG. 25 illustrates a front view of the orthodontic bracket of FIG. 4. Tie wings 28 are formed to include a slot defined by an upper side wall 31, a lower side wall 33, and a bottom surface 30 for receiving a rectangular wire. The slot being aligned at a predetermined torque angle to apply torque forces to a tooth when the rectangular wire is inserted therein. It is important that a center line of bottom surface is positioned correctly on the tooth. However, since the slot is angled, bottom surface 30 extends from line 70 to dotted line 72. Therefore, alignment of the bracket 29 by viewing the front face of bracket 29 can be difficult. Therefore, a marking 74 is formed on a base 76 of bracket 29 indicating the precise location of a center line of bottom surface 30 of the bracket slot. This marking 74 therefore facilitates alignment of bracket 29 on the tooth. Illustratively, marking 74 is a mesial-distal (horizontal) line etched, painted, cast, molded or otherwise on the bracket or bonding pad or welding flange to determine the "coplanar" level slot lineup. Due to the angled torque preadjustments, the slot opening at the bracket face point often gives a misleading impression of level slot lineup, as the slot bottom (hidden from clear view) may lie on a different plane. The line on the bracket, flange or pad should identify the slot base point, represented by the horizontal line, thus allowing for slot base points to be accurately aligned bracket to bracket verses the more inaccurate slot face points. This can be joined with the more common long axis bracket/pad lines illustrated by line 78 (designed to correct express tip preadjustments) to create a "crosshair" effect, thus dramatically heightening the ability to correctly place, and correctly express, built-in bracket preadjustments.

Figure 26:
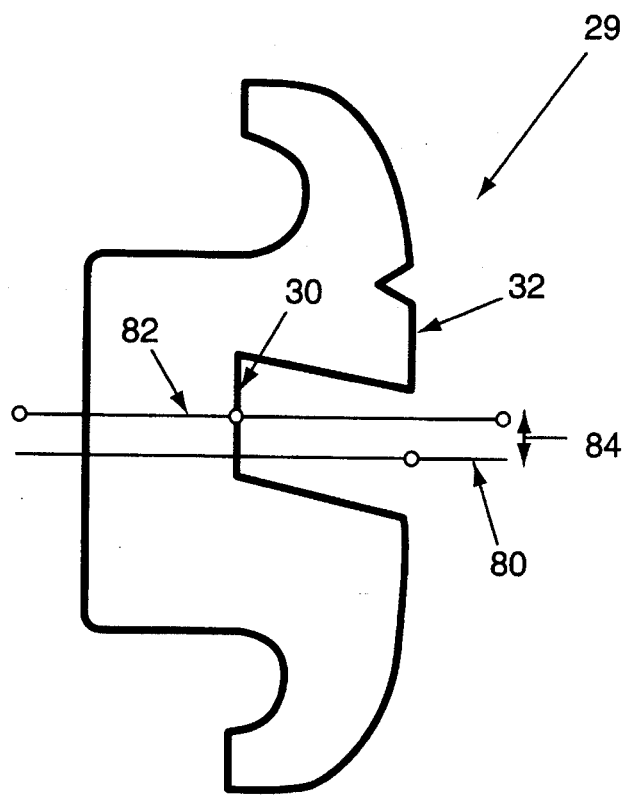
FIG. 26 is a side elevational view of the bracket of FIG. 25 illustrating the distance between a center of the slot opening an the actual center of a bottom surface of the slot.

FIG. 26 illustrates the alignment problem caused if the slot opening adjacent front face 32 of bracket 29 is used for bracket alignment. Line 80 illustrates the location of a mid point of the slot opening adjacent front face 32 of bracket 29. The actual location of a center point of back surface 30 is illustrated by line 82. Therefore, if the slot opening adjacent front face 32 of bracket 29 is used for alignment of bracket 29, alignment of the bracket 29 would be off by distance 84. Marking 74 illustrated in FIG. 25 marks the location of center line 82 to facilitate placement of bracket 29 on a tooth.

Although the invention has been described in detail with reference to a certain preferred embodiment, variations and modifications exist within the scope and spirit of the invention as described and defined in the following claims.

What is claimed is:

1. An orthodontic bracket system for straightening upper central, lateral, cuspid, and bicuspid teeth, the bracket system comprising:

a plurality of rectangular wires having a plurality of different sizes;

an upper bicuspid bracket;

an upper cuspid bracket;

an upper lateral bracket;

an upper central bracket including a 0.020 inch width slot for receiving a selected one of the plurality of rectangular wires therein, the slot being aligned at a torque angle of about +17°.

2. The bracket system of claim 1, wherein the upper lateral bracket includes a 0.020 inch width slot for receiving the selected rectangular wire therein, the slot of the upper lateral bracket being aligned at a torque angle of about +12°.

3. The bracket system of claim 1, wherein the upper cuspid bracket includes, a 0.020 inch width slot for receiving the selected rectangular wire therein, the slot of the upper cuspid bracket being aligned at a torque angle of about 7°.

4. The bracket system of claim 3, wherein the slot formed in the upper cuspid bracket is aligned at a predetermined angulation, and the upper cuspid bracket is reversible so that the slot of the upper cuspid bracket can be aligned at either a −7° or a +7° torque angle relative to the upper cuspid tooth without changing the angulation.

5. The bracket system of claim 1, further comprising an extraction-oriented upper cuspid bracket which includes a 0.020 inch width slot for receiving the selected rectangular wire therein, the slot being aligned at a torque angle of about −4°.

6. The bracket system of claim 1, wherein the upper bicuspid bracket includes a 0.020 inch width slot for receiving a rectangular wire therein, the slot of the upper bicuspid bracket being aligned at a torque angle of about −7°.

7. The bracket system of claim 6, further comprising a second upper bicuspid bracket including a 0.020 inch width slot for receiving a rectangular wire therein, the slot of the second upper bicuspid bracket being aligned at a torque angle of about 11°.

8. An orthodontic bracket system comprising:

a plurality of rectangular wires having a plurality of different sizes;

an upper bicuspid bracket;

an upper cuspid bracket;

an upper lateral bracket;

an upper central bracket including means for applying any actual torque force to an upper central tooth in a range of actual torque forces from about 0° to about +10° to an upper central tooth.

9. The bracket system of claim 8, wherein the means for applying any actual torque force to an upper central tooth is configured to apply any actual torque force to an upper central tooth in a range of actual torque forces from about 0° to about +14° to an upper central tooth.

10. The bracket system of claim 8, wherein the means for applying any actual torque force to an upper central tooth includes a slot formed in the upper central bracket for engaging a selected rectangular wire inserted therein, the slot having a width of 0.020 inch, and the slot being aligned at a torque angle of about +17°.

11. The bracket system of claim 8, wherein the upper lateral bracket includes means for applying any actual torque force to an upper lateral tooth in a range of actual torque forces from about 0° to about +6° to an upper lateral tooth.

12. The bracket system of claim 11, wherein the means for applying any actual torque force to an upper lateral tooth includes a slot formed in the upper lateral bracket for engaging a selected rectangular wire inserted therein, the slot having a width of 0.020 inch, and the slot being aligned at a torque angle of about +12°.

13. The bracket system of claim 8, wherein the means for applying any actual torque force to an upper lateral tooth is configured to apply any actual torque force to an upper lateral tooth in a range of actual torque forces from about 0° to about +9° to an upper lateral tooth.

14. The bracket system of claim 8, wherein the upper cuspid bracket includes means for applying both positive and negative torque forces to an upper cuspid tooth.

15. The bracket system of claim 8, wherein the upper cuspid bracket includes means for applying any actual torque force to an upper cuspid tooth in a range of actual torque forces from about −4° to about +4° to an upper cuspid tooth.

16. The bracket system of claim 15, wherein the means for applying any actual torque force to an upper cuspid tooth includes a slot formed in the upper cuspid bracket for engaging a selected rectangular wire inserted therein, the slot having a width of 0.020 inch, and the slot being aligned at a torque angle of about 7° and at a predetermined angulation, the upper cuspid bracket being reversible on the upper cuspid tooth so that the slot can be aligned at a −7° torque angle or a +7° torque angle without changing the angulation.

17. The bracket system of claim 8, further comprising an extraction-oriented upper cuspid bracket which includes a 0.020 inch width slot for receiving the selected rectangular wire therein, the slot being aligned at a torque angle of about −4°.

18. The bracket system of claim 8, wherein the upper bicuspid bracket includes means for applying any actual torque force to an upper bicuspid tooth in a range of actual torque forces from about 0° to about −5°.

19. The bracket system of claim 8, further comprising a second upper bicuspid bracket including means for applying any actual torque range to an upper bicuspid tooth in a range of actual torque forces from about 0° to about −8°.

20. The bracket system of claim 8, further comprising a preformed, adjustable utility torquing arch for increasing torque forces applied by the bracket system.

21. The bracket system of claim 8, wherein a 0.016 inch by 0.016 inch square wire engages a slot formed in each bracket to provide a passive borderline of the bracket system, thereby reducing crown drift without delivering any correction.

22. The bracket system of claim 8, further comprising a lower bicuspid bracket, a lower cuspid bracket, and a lower anterior bracket.

23. The bracket system of claim 22, wherein the lower bicuspid bracket, the lower cuspid bracket, and the lower anterior bracket are each formed to include a 0.020 inch width slot for receiving a selected one of the plurality of rectangular wires therein, the slot in the lower bicuspid bracket being aligned at a torque angle of about −17°, the slot in the lower cuspid bracket being aligned at a torque angle of about 7° and the slot in the lower anterior bracket being aligned at a torque angle of about 0°.

24. An orthodontic bracket system for use with a rectangular wire, the bracket system comprising a plurality of brackets including an upper bicuspid bracket, an upper cuspid bracket, an upper lateral bracket, an upper central bracket, a lower bicuspid bracket, a lower cuspid bracket, and a lower anterior bracket, each of the plurality of brackets including a 0.020 inch width slot aligned at a selected torque angle for receiving the rectangular wire therein.

25. The bracket system of claim 24, wherein the upper central bracket includes means for applying any actual torque force to an upper central tooth in a range of actual torque forces from about 0° to about +10°, the upper lateral bracket includes means for applying any actual torque force to an upper lateral tooth in a range of actual torque forces from about 0° to about +6°, the upper cuspid bracket includes means for applying any actual torque force to an upper cuspid tooth in a range of actual torque forces from about 4° to about +4°, and the upper bicuspid bracket includes means for applying any actual torque force to an upper bicuspid tooth in a range of actual torque forces from about 0° to about −5°.

26. The bracket system of claim 25, wherein the means for applying any actual torque force to an upper central tooth is configured to apply any actual torque force to an upper central tooth in a range of actual torque forces from about 0° to about +14° to an upper central tooth.

27. The bracket system of claim 25, wherein the means for applying any actual torque force to an upper lateral tooth is configured to apply any actual torque force to an upper lateral tooth in a range of actual torque forces from about 0° to about +9° to an upper lateral tooth.

28. In an orthodontic bracket having a front bracket face including a slot defined by an upper side wall, a lower side wall, and a bottom surface having an imaginary center line midway between said side walls for receiving a rectangular wire therein, the slot being aligned at a predetermined torque angle to apply torque forces to a tooth when the rectangular wire is inserted therein, the improvement comprising a marking formed on the bracket aligned with said center line of the bottom surface of the slot to provide an indication of the position of the center line of the bottom surface relative to the front bracket face, thereby facilitating alignment of the bracket on the tooth.

29. The improvement of claim 28, wherein the marking is formed on a base of the bracket.

* * * * *